(12) United States Patent
Oba et al.

(10) Patent No.: US 10,031,457 B2
(45) Date of Patent: Jul. 24, 2018

(54) OPTICAL SENSOR, RECORDING MEDIUM DISCRIMINATION DEVICE, AND IMAGE FORMING APPARATUS

(71) Applicants: Yoshihiro Oba, Miyagi (JP); Fumikazu Hoshi, Miyagi (JP); Kazuma Goto, Miyagi (JP); Yoshihiro Misaka, Miyagi (JP)

(72) Inventors: Yoshihiro Oba, Miyagi (JP); Fumikazu Hoshi, Miyagi (JP); Kazuma Goto, Miyagi (JP); Yoshihiro Misaka, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 99 days.

(21) Appl. No.: 15/001,852

(22) Filed: Jan. 20, 2016

(65) Prior Publication Data

US 2016/0209794 A1   Jul. 21, 2016

(30) Foreign Application Priority Data

Jan. 21, 2015 (JP) ................................ 2015-009553
Nov. 25, 2015 (JP) ................................ 2015-230009

(51) Int. Cl.
*H04N 1/06* (2006.01)
*G01N 21/21* (2006.01)
(Continued)

(52) U.S. Cl.
CPC ......... *G03G 15/5029* (2013.01); *G01N 21/21* (2013.01); *H04N 1/0032* (2013.01);
(Continued)

(58) Field of Classification Search
CPC ............... G01N 21/21; G03G 15/5029; G03G 2215/132; G03G 2215/616; H04H 1/06; H04H 1/0032; H04H 1/00204
See application file for complete search history.

(56) References Cited

U.S. PATENT DOCUMENTS 7,655,936 B2 * 2/2010 Sawayama ............. G01N 21/55
250/559.4
2008/0246623 A1 * 10/2008 Nagashima ............ G01N 21/21
340/630
(Continued)

FOREIGN PATENT DOCUMENTS

JP     2005083850 A  *  3/2005 ............ B41J 11/009
JP     2005156380 A  *  6/2005
JP     2012127937 A  *  7/2012

*Primary Examiner* — Dominic J Bologna
(74) *Attorney, Agent, or Firm* — Cooper & Dunham LLP

(57) ABSTRACT

An optical sensor including an irradiation system including an irradiation system including a light source unit having a light source, the irradiation system configured to emit a linearly polarized light of a first polarization direction onto a surface of an object, a polarizing optical element disposed on an optical path of the light that is emitted from the irradiation system and reflected by diffuse reflection from an incident plane of the object and configured to separate a linearly polarized light component of a second polarization direction, a first photodetector configured to receive the linearly polarized light component of the second polarization direction separated by the polarizing optical element, and a housing supporting the irradiation system, the polarizing optical element, and the first photodetector, where the light source unit is fixed to the housing in a light emitting direction of the light source unit via space.

19 Claims, 21 Drawing Sheets

(51) Int. Cl.
*H04N 1/00* (2006.01)
*G03G 15/00* (2006.01)
(52) U.S. Cl.
CPC ........... *H04N 1/00204* (2013.01); *H04N 1/06* (2013.01); *G03G 2215/00616* (2013.01); *G03G 2215/00751* (2013.01); *G03G 2215/0132* (2013.01)

(56) References Cited

U.S. PATENT DOCUMENTS

| | | |
|---|---|---|
| 2012/0134693 A1 | 5/2012 | Hoshi et al. |
| 2013/0022363 A1* | 1/2013 | Naka ............... G03G 15/5058 399/49 |
| 2013/0057861 A1* | 3/2013 | Ishii ............... G01N 21/4738 356/369 |
| 2013/0057868 A1 | 3/2013 | Oba et al. |
| 2013/0194573 A1 | 8/2013 | Ohba et al. |
| 2013/0216245 A1 | 8/2013 | Hoshi et al. |
| 2013/0216246 A1* | 8/2013 | Hoshi ............... G03G 15/6591 399/45 |
| 2013/0216247 A1 | 8/2013 | Oba et al. |
| 2013/0228674 A1 | 9/2013 | Oba et al. |
| 2013/0235377 A1 | 9/2013 | Ishii et al. |
| 2014/0241742 A1 | 8/2014 | Hoshi et al. |
| 2014/0246590 A1 | 9/2014 | Ishii et al. |
| 2014/0268151 A1 | 9/2014 | Ohba et al. |
| 2015/0015882 A1 | 1/2015 | Goto et al. |
| 2015/0261163 A1 | 9/2015 | Ishii et al. |

* cited by examiner

OPTICAL SENSOR, RECORDING MEDIUM DISCRIMINATION DEVICE, AND IMAGE FORMING APPARATUS

CROSS-REFERENCE TO RELATED APPLICATIONS

This patent application is based on and claims priority pursuant to 35 U.S.C. § 119(a) to Japanese Patent Application Nos. 2015-009553 and 2015-230009, filed on Jan. 21, 2015, and Nov. 25, 2015, respectively, in the Japan Patent Office, the entire disclosure of which is hereby incorporated by reference herein.

BACKGROUND

Technical Field

Embodiments of the present invention relate to an optical sensor, a recording medium discrimination device, and an image forming apparatus.

Background Art

Some image forming apparatuses, which form an image on a recording medium using an ink or toner, use an optical sensor to determine the brand, the surface condition, or the like of the recording medium. Some optical sensors irradiate the recording medium with the linearly polarized light (S-polarized light) emitted from an irradiation system, and detect the amount of the light changed from the S-polarized light to the P-polarized light due to the reflection on the recording medium using a photodetector and receive the components of the light where the polarization has been changed using a photodetector. By so doing, such optical sensors can detect multiple-diffuse reflection light or internal diffusion reflection light.

SUMMARY

Embodiments of the present invention described herein provide an optical sensor, a recording medium discrimination device, and an image forming apparatus. The optical sensor includes an irradiation system including a light source unit having a light source, the irradiation system configured to emit a linearly polarized light of a first polarization direction onto a surface of an object, in an incident direction inclined with reference to a normal-line direction of the surface of the object, a polarizing optical element disposed on an optical path of the light that is emitted from the irradiation system and reflected by diffuse reflection from an incident plane of the object and configured to separate a linearly polarized light component of a second polarization direction from the light emitted from the irradiation system, the second polarization direction being orthogonal to the first polarization direction, a first photodetector configured to receive the linearly polarized light component of the second polarization direction separated by the polarizing optical element, and a housing supporting the irradiation system, the polarizing optical element, and the first photodetector, where the light source unit is fixed to the housing in a light emitting direction of the light source unit via space. The recording medium discrimination device includes the optical sensor and a processor configured to discriminate the object based on a signal output from the optical sensor. The image forming apparatus includes an image forming unit configured to form an image on a recording medium, and the recording medium discrimination device, where the object is the recording medium.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

Figure 1:
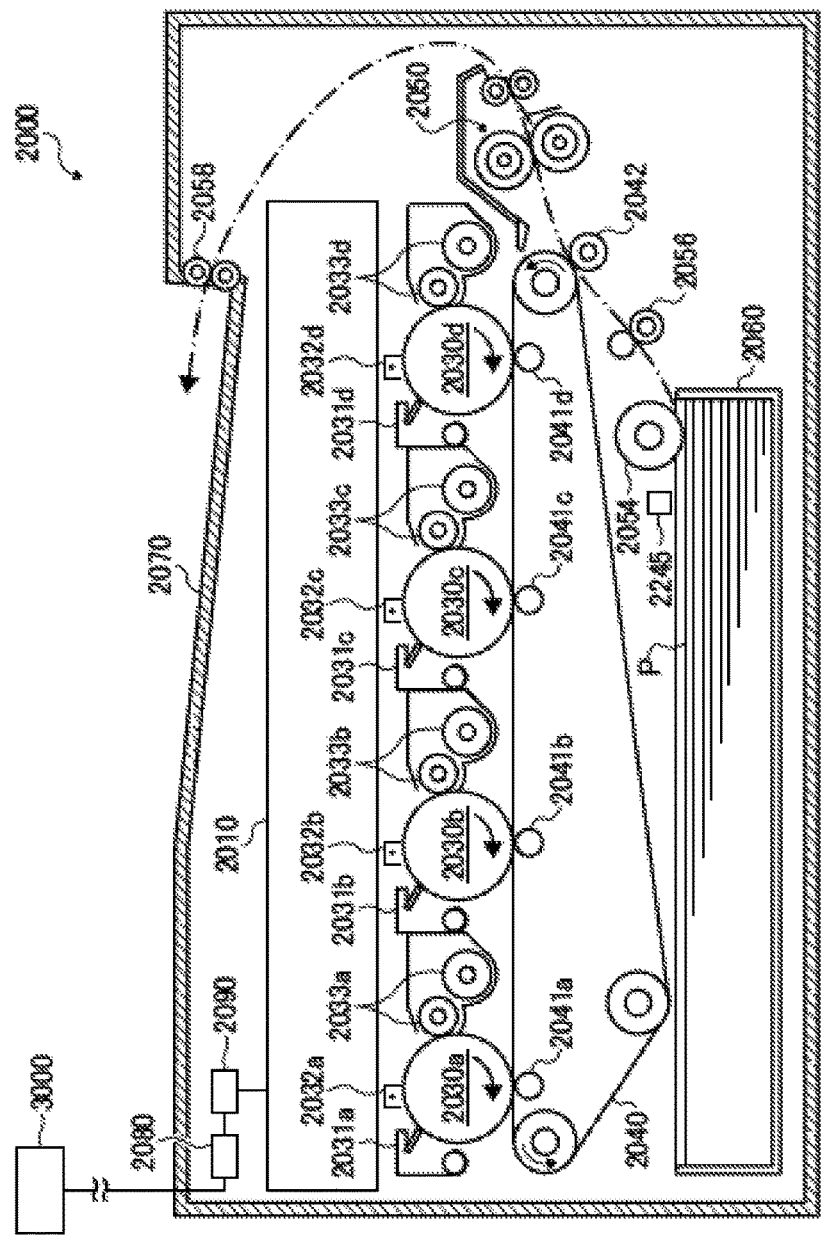
FIG. 1 is a schematic diagram the configuration of a color printer according to an embodiment of the present invention.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, an embodiment and a modification of the present invention are described one by one with reference to the drawings. In the description of the embodiments and modifications, like reference signs are given to elements having similar functionality or configuration, and overlapping description may be omitted. The drawings may be simplified or partially omitted to aid the understanding of a particular configuration.

FIG. 1 illustrates an outline of the configuration of a color printer 2000 that serves as an image forming apparatus according to an embodiment of the present invention. The color printer 2000 according to the present embodiment is a tandem-type multicolor printer that forms a full-color toner image by superimposing multiple images of four colors (black, cyan, magenta, and yellow) on top of one another. The color printer 2000 includes, for example, an optical scanner 2010, photoconductor drums (2030a, 2030b, 2030c, and 2030d) that serve as four image bearers, four cleaning units (2031a, 2031b, 2031c, and 2031d), four charging devices (2032a, 2032b, 2032c, and 2032d), developing rollers (2033a, 2033b, 2033c, and 2033d) that serve as four developer bearers, a transfer belt 2040 looped over rollers that serve as a plurality of rotation supports, transfer rollers (2041a, 2041b, 2041c, and 2041d) that serve as primary transferors, a secondary transfer roller 2042 that serves as a secondary transferor, a fixing device 2050, a sheet feeding roller 2054 and an output roller pair 2058 that serve as a medium conveying member, a sheet feeding tray 2060 and an output tray 2070, a communication controller 2080, an optical sensor 2245, and a control circuit 2090 that controls the elements as described above in a centralized manner. The communication controller 2080 controls bidirectional communication with a host device 3000 (for example, a personal computer (PC)) through a network or the like.

The photoconductor drum 2030a, the charging device 2032a, the developing roller 2033a, and the cleaning unit 2031a are used as a unit, and together configure an image forming station that forms a black image. The photoconductor drum 2030b, the charging device 2032b, the developing roller 2033b, and the cleaning unit 2031b are used as a unit, and together configure an image forming station that forms a cyan image.

The photoconductor drum 2030c, the charging device 2032c, the developing roller 2033c, and the cleaning unit 2031c are used as a unit, and together configure an image forming station that forms a magenta image. The photoconductor drum 2030d, the charging device 2032d, the developing roller 2033d, and the cleaning unit 2031d are used as a unit, and together configure an image forming station that forms a yellow image.

A photosensitive layer is formed on the surface of each of the photoconductor drums (2030a, 2030b, 2030c, and 2030d). In other words, the surface of each of the photoconductor drums is scanned. The photoconductor drums (2030a, 2030b, 2030c, and 2030d) are rotated by a driver in the direction of the arrows as illustrated in FIG. 1. Each of the charging devices (2032a, 2032b, 2032c, and 2032d) evenly charges the surface of the associated photoconductor drum. The optical scanner 2010 scans each of the surfaces of the electrically-charged photoconductor drums, with the light that is modulated for each color based on the multicolor image data (i.e., black image data, cyan image data, magenta image data, and yellow image data) received from the control circuit 2090.

Accordingly, a latent image that corresponds to the image data of each color is formed on the surface of each of the photoconductor drums (2030a, 2030b, 2030c, and 2030d). Each of the latent images formed as above moves towards the corresponding developing roller (2033a, 2033b, 2033c, or 2033d) as the photoconductor drum (2030a, 2030b, 2030c, or 2030d) rotates. A toner from the corresponding toner cartridge, which serves as a developer, is thinly and evenly applied to the surface of each of the developing rollers (2033a, 2033b, 2033c, and 2033d) as it rotates. Then, the toner that has been applied to the surface of each of the developing rollers (2033a, 2033b, 2033c, and 2033d) moves and adheres to the portions of the surface of the corresponding photoconductor drum that are irradiated with light by the optical scanner 2010. In other words, each of the developing rollers (2033a, 2033b, 2033c, and 2033d) renders a latent image manifest by making the toner adhere to the latent image formed on the surface of the corresponding photoconductor drum (2030*a*, 2030*b*, 2030*c*, and 2030*d*). Each of the toner images moves towards the transfer belt 2040 as the photoconductor drum (2030*a*, 2030*b*, 2030*c*, or 2030*d*) rotates. Each of the toner images of yellow, magenta, cyan, and black is sequentially primarily transferred to the transfer belt 2040 at a site facing the corresponding transfer roller (2041*a*, 2041*b*, 2041*c*, or 2041*d*) with specified timing. Then, the primarily-transferred toner images are superimposed on top of one another to form a multicolor image.

The sheet feeding tray 2060 stores the sheet P therein. The sheet feeding roller 2054 is disposed near the sheet feeding tray 2060, and the sheet feeding roller 2054 pulls out the sheet P on a one-by-one basis from the sheet feeding tray 2060. The pulled out sheet P is fed by the registration roller pair 2056 towards a secondary transfer unit formed at the space between the transfer belt 2040 and the secondary transfer roller 2042 with prescribed timing. Then, the toner image on the transfer belt 2040 is transferred to the sheet P at the secondary transfer unit, and is sent to the fixing device 2050.

At the fixing device 2050, heat and pressure are applied to the sheet P to fix the toner on the sheet P. The sheet P on which the toner has been fixed is conveyed to the output tray 2070 through the output roller pair 2058, and the sheet P is stacked on one another in sequence.

Each of the cleaning units (2031*a*, 2031*b*, 2031*c*, and 2031*d*) removes the transferred toner (residual toner) remaining on the surface of the corresponding photoconductor drum. The surface of the photoconductor drum from which the residual toner has been removed moves back again to a position where the surface of the photoconductor drum faces the corresponding charging device.

As described above, the color printer 2000 form an image by transferring a toner image on the surface Pa of the sheet P, i.e., a sheet-like recording medium typified by a printing paper, and by heating and pressurizing the recording medium using the fixing device 2050 for fixation under certain specified conditions. When an image is formed, printing conditions such as a level of heating and pressure at the time of fixing, which is an example of a condition for image formation, should be taken into consideration. When a high-quality image is to be formed, in particular, the conditions for image formation need to be set on an individual basis according to the brand (type) of the sheet P. This is because the quality of the image on the sheet P is heavily dependent on the material, thickness, moisture content, smoothness, coating state, or the like of the sheet P. Concerning the smoothness, for example, the stability of a toner becomes low at concave portions of the surface of the sheet when a proper fixation condition is not chosen. For example, irregularities in color may develop if fixing conditions are not proper for the type of the sheet P.

Further, due to the development of image forming apparatuses and the diversification of expression in recent years, several hundred or more types of printing paper have become available as the sheet P, and a number of brands exist for each of these types for varying specifications such as different basis weights and thickness. Note that in the following description, the most detailed classification of the sheet P, into which varying specifications such as different basis weights and thickness are taken into consideration, may be referred to as a brand, and the discrimination of the brand may be referred to as a brand-level discrimination. In order to achieve high-quality image formation, detailed conditions for image formation needs to be set for every one of these brands.

In recent years, as a recording medium, the number of brands of paper is increasing for plain paper, coated paper typified by gloss-coated paper, matte coated paper, and art paper, plastic sheet, and special paper whose surface is embossed.

The color printer 2000 includes the optical sensor 2245 that irradiates the sheet P with light and receives the reflected light to optically detect the sheet P. The optical sensor 2245 is used to determine the brand of the sheet P accommodated inside the sheet feeding tray 2060. Note that the optical sensor 2245 may separately be provided outside the sheet feeding tray 2060, as a discrete recording medium detector.

Figure 22:
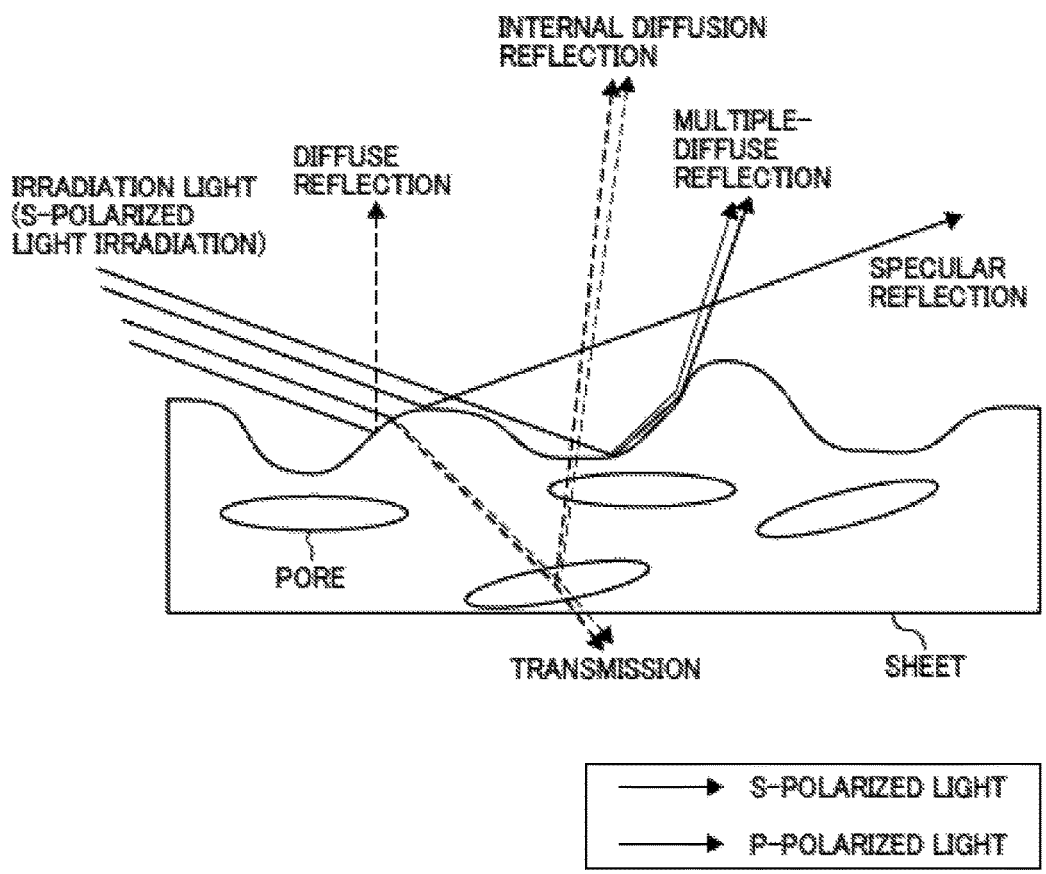
FIG. 22 is a diagram illustrating the changes in polarization due to the reflection on a recording medium and the classification of the types of the reflection, according to an embodiment of the present invention.

FIG. 22 is a diagram illustrating the changes in polarization due to the reflection on a recording medium and the classification of the types of the reflection, according to an embodiment of the present invention. Here, the light reflected from the sheet is described with reference to FIG. 22. The light reflected may be classified into two kinds of reflected light, consisting of the light reflected by the surface of the sheet and the light reflected inside the sheet. On one hand, the light that is reflected by the surface of the sheet can further be classified into three kinds of reflected light, consisting of the reflection light obtained by specular reflection, the light reflected towards a diffuse direction obtained by one-time single reflection, and light reflected towards a diffuse direction obtained by multiple reflections on the bumps and dips of the surface of the paper. For the purpose of simplification, in the following description, these three types of reflection light are referred to simply as "specular reflection light", "diffuse reflection light", and "multiple-diffuse reflection light". On the other hand, the light reflected inside the sheet (in the following description, such light is referred to as "internal diffusion reflection light") repeats being reflected a number of times at places such as inner fibers and the interface of pores when the sheet is a general-purpose printing paper. Accordingly, the reflection directions are assumed to have isotropy, and the intensity distribution can approximate to the Lambert's law of distribution. As a result, the light that is reflected from the sheet can be classified into specular reflection light, diffuse reflection light, multiple-diffuse reflection light, and internal diffusion reflection light.

The polarization directions of the specular reflection light and the diffuse reflection light are equivalent to the polarization direction of the irradiation light. By contrast, the multiple-diffuse reflection light and the internal diffusion reflection light include a polarized component orthogonal to the polarization direction of the irradiation light. Note that the polarization direction rotates on the surface of the sheet only when the irradiation light is reflected on a part of the surface that is inclined in the direction of the rotation with reference to direction of travel.

The optical sensor that discriminates the brand of sheet disclosed in JP-2012-127937-A irradiates the sheet with the linearly polarized light (S-polarized light), and detects the amount of the light changed from the S-polarized light to the P-polarized light due to the reflection on the recording medium. The light components where the polarization has been changed are received to detect the multiple-diffuse reflection light and the internal diffusion reflection light, and the volumes of the detected multiple-diffuse reflection light and internal diffusion reflection light are used as parameters for discriminating the brand.

In the following description where the polarized light changing due to the reflection on the sheet is referred to, basically, the irradiation light is referred to as the S-polarized light, and the light component changed due to the reflection is referred to as the P-polarized light. However, no limitation is indicated thereby, and the irradiation light may be the P-polarized light, and the S-polarized light component changed due to the reflection may be detected in an optical sensor according to an alternative embodiment.

For the cost reduction purposes, the polarization ratio of the light source is not high in commonly-used optical sensors that discriminate the sheet. For example, even a light source that is supposed to emit linearly polarized light may emit limit that includes an inversely-polarized component. In other words, the light source of a known optical sensor is not a light source that perfectly emits only the S-polarized light, but the light emitted from such a light source includes the P-polarized light. In cases where the light emitted from the light source includes a P-polarized light component, if the P-polarized light component originating from the light source is detected as a diffuse reflection light rather than the polarized light component changed due to the reflection (multiple-diffuse reflection or internal diffusion reflection) on the sheet to be discriminated, an appropriate discrimination becomes difficult to achieve. For this reason, the configuration in which the P-polarized light component originating from the light source is excluded as much as possible, for example, the configuration in which no detection is performed in a detection direction near the specular reflection, is desired to detect changes in polarized light.

However, it is necessary to improve the polarization ratio of the light source in order to perfectly exclude the P-polarized light component originating from the light source to an undetectable level for an optical sensor. This also leads to increases in cost. In view of the above circumstances, the reproducibility of the polarization ratio of the light source is improved for the individual optical sensor to improve the accuracy, while the optical sensor still detects the P-polarized light component originating from the light source. In other words, the discrimination can be achieved as long as the reproducibility of the polarization ratio is high for the individual optical sensor. In the sheet-type discrimination system, a situation is to be avoided in which the amount of the P-polarized light component originates from the light source varies for each of the optical sensors. It is satisfactory as long as the P-polarized light components originating from the light source included in the output of the optical sensor that has generated a table and the output of a mass-produced optical sensor is reproduced. For these reasons, it is desired for optical sensors to reduce the variations in the output of the optical sensors due to the differences in the polarization ratio.

There are three major elements that have an impact on the polarization characteristics, including the compressive stress onto the light source unit, the amounts of the light that is emitted, and the steadiness of the installation position of the optical system. As known in the art, the polarization ratio of a light source such as a semiconductor laser changes when an external compressive stress is applied to the elements of the light source. This is because, for example, a structure in which a slit is formed in one direction near the emitting position of the laser is adopted to stabilize the polarization of the elements of the light source, and such a structure is deformed by externally applied compressive stress.

Moreover, it is known in the art that the amount of the emitted light correlates with the polarization ratio in a light source such as a semiconductor laser.

The polarization ratio also changes according to the installed position of the optical system. This is due to the error in the assembly of the light source and other elements that together configure an optical sensor. The direction of the linearly polarized light emitted from the light source is determined by the object plane to be irradiated with the light or relative positions of the direction of the linearly polarized light and the polarization direction in which the photoreceptor receives the light. For example, as illustrated in FIG. 22, when the light source is assembled to a position displaced from the installation position in design in the rotation direction of the light beam, the object to be irradiated with light receives the P-polarized light in an amount greater than the amount originating from the characteristics of the light source itself.

Figure 23A:
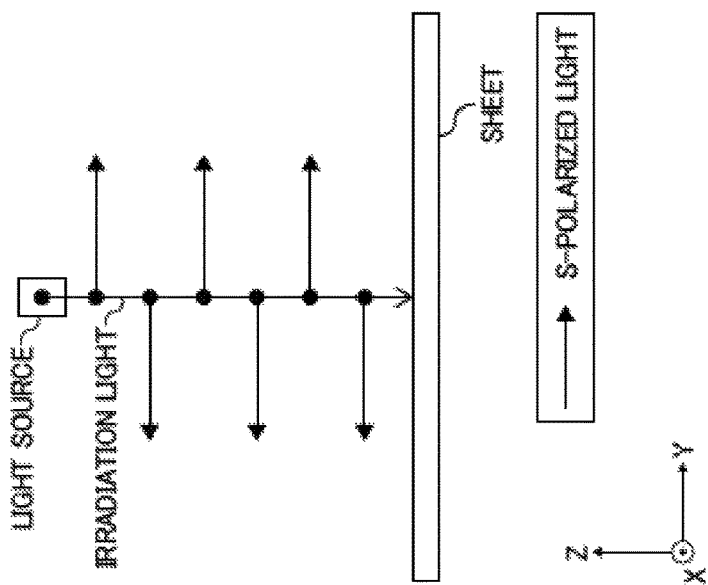
FIG. 23A and FIG. 23B are diagrams illustrating the changes in polarization ratio depending on the installation of a light source.

FIG. 23A is a diagram illustrating an example in which the light source is properly installed and the object plane can be irradiated with only the linearly polarized light of the S-polarized light.

Figure 23B:
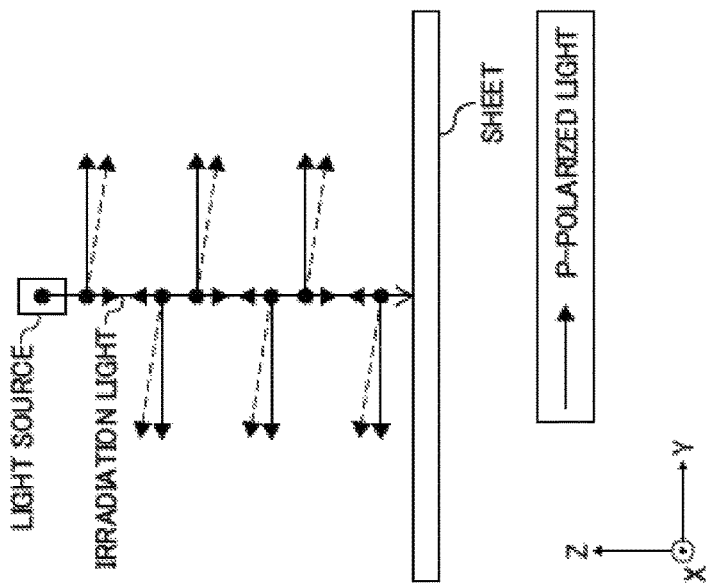

FIG. 23B is a diagram illustrating an example in which the light source is assembled to a position displaced in the rotation direction of the light beam of the light source and the object plane is irradiated with the linearly polarized light of both the S-polarized light and the P-polarized light.

In the optical sensor according to the present embodiment, by way of example, the P-polarized light component that is included in the diffuse reflection light caused when the sheet is irradiated with the S-polarized light is used as a means for discriminating the brand of the sheet. This is because the P-polarized light component is a component where the polarization is changed for the first time due to the reflection on the sheet P, and the P-polarized light component serves as a useful index that indicates the degree of the scattering of the light reflection on the sheet P. In other words, the P-polarized light component is information unique to the object which can be used to discriminate brand of the sheet. However, for the factors described as above, there are variations in the polarization ratio of an optical sensor, and the amount of the P-polarized light component originating from the light source varies. The P-polarized light component originating from the light source are detected by a photodetector together with the P-polarized light component caused by the reflection on the sheet P.

First Embodiment

Figure 2:
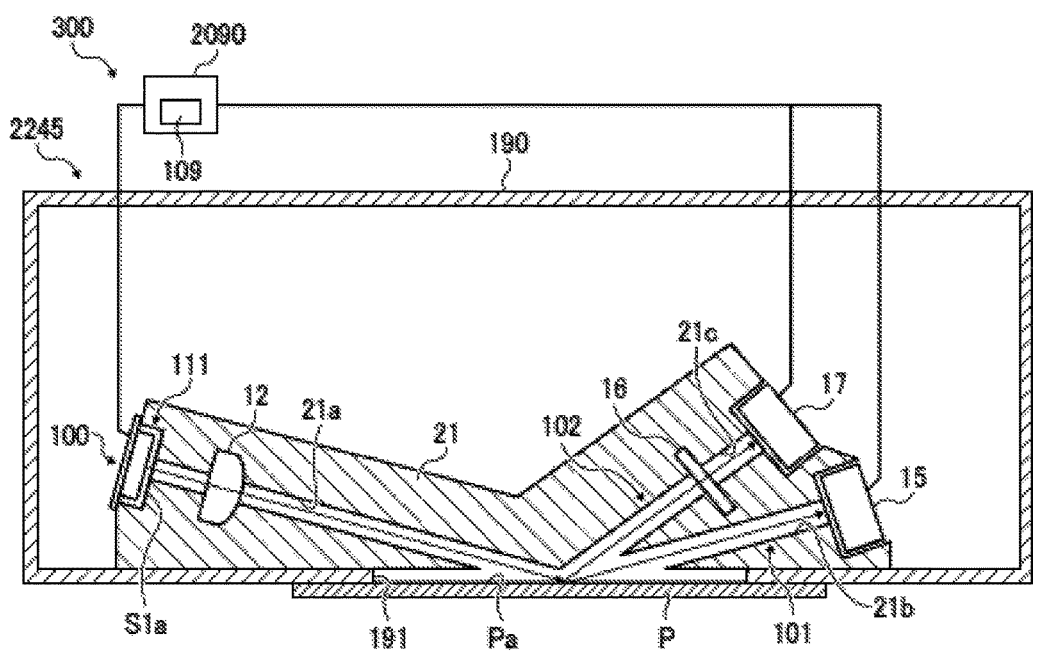
FIG. 2 is a diagram illustrating the configuration of an optical sensor according to a first embodiment of the present invention.
Figure 2:
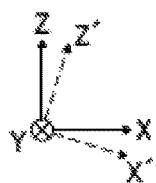

FIG. 2 is a diagram illustrating the configuration of an optical sensor according to a first embodiment of the present invention. As illustrated in FIG. 2, the optical sensor 2245 according to the present embodiment includes an irradiation system 100, a second light detection system 101, a first light detection system 102, a collimator lens 12, a housing 21 maintaining relative positions of these components, and a dark box 190 accommodating these components. The housing 21 and the dark box 190 may be a component in common or different components. The dark box 190 is a box made of metal such as aluminum, and the surface of the dark box 190 is anodized in black in order to reduce the influence of disturbance light and stray light. Note that the material of the dark box 190 is not limited in the present embodiment, and may be made of resin. The dark box 190 has an opening 191 formed to irradiate the surface Pa of the sheet P, i.e., the surface of the object, with the irradiation light emitted from the irradiation system 100.

The irradiation system 100 emits a linearly polarized light of a first polarization direction onto the surface Pa of the sheet P, in an incident direction inclined with reference to the normal-line direction of the surface Pa of the sheet P. The collimator lens 12 is disposed on the optical path (opening hole 21a) of the light emitted from the irradiation system 100 in a fixed manner.

In the housing 21, the opening hole 21a, an opening hole 21b, and an opening hole 21c that guide the light emitted from the irradiation system 100 to the opening 191 are formed. The opening hole 21b is the path through which the light reflected on the surface Pa of the sheet P below the opening 191 by specular reflection passes through, and the opening hole 21c is the path through which the light reflected on the surface Pa of the sheet P (on the incident plane of the sheet P) by diffuse reflection passes through. The collimator lens 12 is disposed on the optical path (opening hole 21a) of the light emitted from the irradiation system 100 in a fixed manner to the housing 21.

The second light detection system 101 includes a photoreceptor 15 that is disposed on the optical path (opening hole 21a) of the light emitted from the irradiation system 100 and reflected at the surface Pa of the sheet P by specular reflection, and the photoreceptor 15 serves as a second photodetector that receives the light obtained by specular reflection.

The first light detection system 102 includes a polarizing filter 16 that is disposed on the optical path (opening hole 21c) of the light reflected on the surface Pa of the sheet P (on the incident plane of the sheet P) by diffuse reflection, and the polarizing filter 16 serves as a polarizing optical element that separates the linearly polarized light components in the second polarization direction that is orthogonal to first polarization direction. The first light detection system 102 includes a photoreceptor 17 that serves as a first photodetector that receives the linearly polarized light components separated by the polarizing filter 16 in the second polarization direction. The polarizing filter 16 is disposed on the optical path (opening hole 21c) of the light that is reflected by diffuse reflection in the direction of the normal line drawn from the surface Pa of the sheet P, and is fixed to the housing 21.

The processor 109 discriminates the sheet P based on the signals output from the photoreceptor 15 and the photoreceptor 17. In the present embodiment, the optical sensor 2245 and the processor 109 are separately provided, and these optical sensor 2245 and processor 109 together configure a recording medium discrimination device 300 (see FIG. 1). In other words, the color printer 2000 that serves as an image forming apparatus includes the recording medium discrimination device 300.

Note that the optical sensor 2245 and the processor 109 may be formed as a single integrated unit, rather than being separately provided. In this configuration, the optical sensor 2245 provided with the processor 109 may serve as a recording medium discrimination member. In the present embodiment, the processor 109 is disposed inside the control circuit 2090.

In the XYZ three-dimensional orthogonal coordinate system as illustrated in FIG. 2, it is assumed that the direction orthogonal to the surface Pa of the sheet P is the Z-axis direction and the plane parallel to the surface Pa of the sheet P is the XY plane. Moreover, it is assumed that the optical sensor 2245 is disposed, for example, on the +Z side of the sheet P. In the following description, the center of the irradiated area on the surface Pa of the sheet P is referred to simply as an irradiation center. Moreover, the light that has passed through the collimator lens 12 is referred to as irradiation light.

Assuming that the light is incident on the boundary surface of the sheet P, the plane that includes the incident light beam and the normal line drawn from the point of incidence of the boundary surface is referred to as incident plane. In the incident plane according to the present embodiment, it is assumed that the direction parallel to the incident light beam is the X'-axis direction, and that the direction orthogonal to the incident light beam is the Z'-axis direction. In the following description of the embodiments, the terms "S-polarized light" and "P-polarized light" are used not only for the incident light on the sheet P but also for the reflection light. This is for the sake of explanatory convenience, and the light whose polarization direction is the same as that of the incident light (i.e., S-polarized light the present embodiment) on an incident plane is referred to as the S-polarized light, and the light whose polarization direction is orthogonal to the S-polarized light is referred to as the P-polarized light. These terms are used with reference to the polarization direction of the incident light on the sheet P. Note also that the light emitting direction of the light source is referred to as the X'-axis direction, and the axis of the light emitting direction of the light source is referred to as the X' axis, in the present embodiment.

Figure 3:
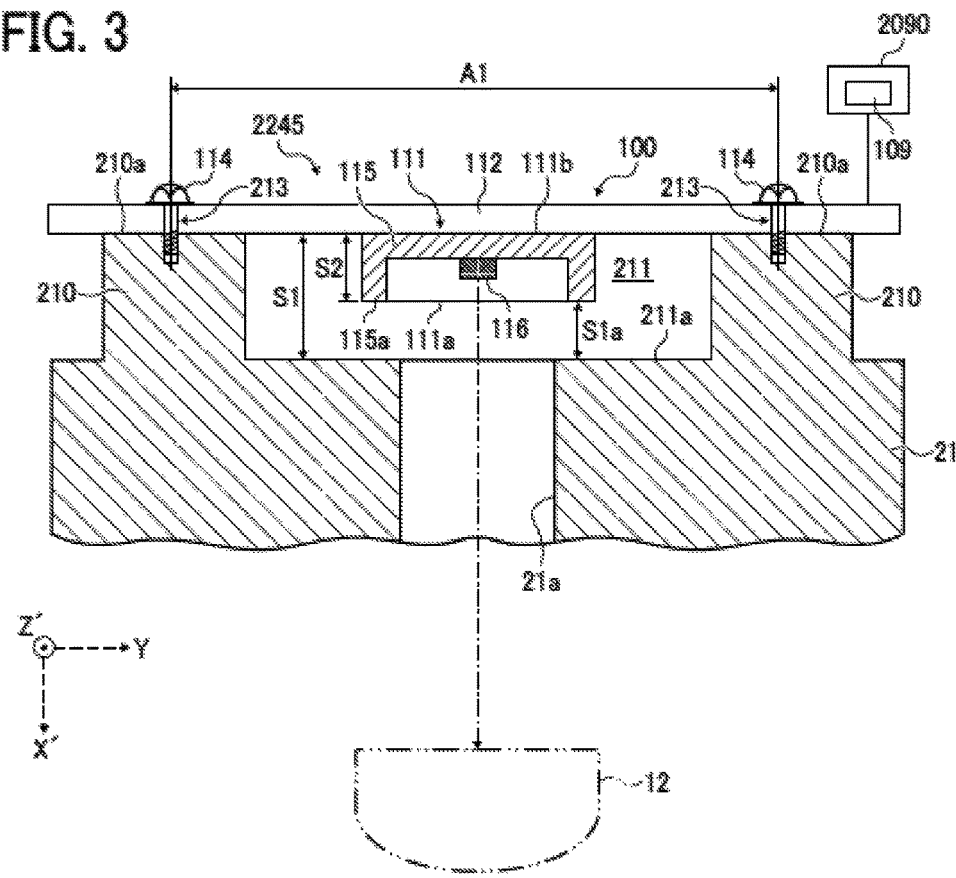
FIG. 3 is a diagram illustrating the configuration of an irradiation system and a housing of the optical sensor according to the first embodiment of the present invention.

FIG. 3 is a diagram illustrating the configuration of the irradiation system 100 and the housing 21 of the optical sensor 2245 according to the first embodiment.

In the present embodiment, as illustrated in FIG. 3, the irradiation system 100 includes a light source unit 111 that emits light, and a circuit board 112 on which the light source unit 111 is mounted. The optical sensor 2245 is connected to the control circuit 2090 through the circuit board 112, and the control circuit 2090 serves as a controller that controls the light source unit 111. In the present embodiment, the control circuit 2090 serves as a controller. However, another controller that controls the light source unit 111 may be provided, separately from the control circuit 2090.

The light source unit 111 is attached to the housing 21 so as to face an end of the opening hole 21a formed in the housing 21. The light source unit 111 includes a package 115, and a light source 116 mounted on the package 115.

Figure 4:
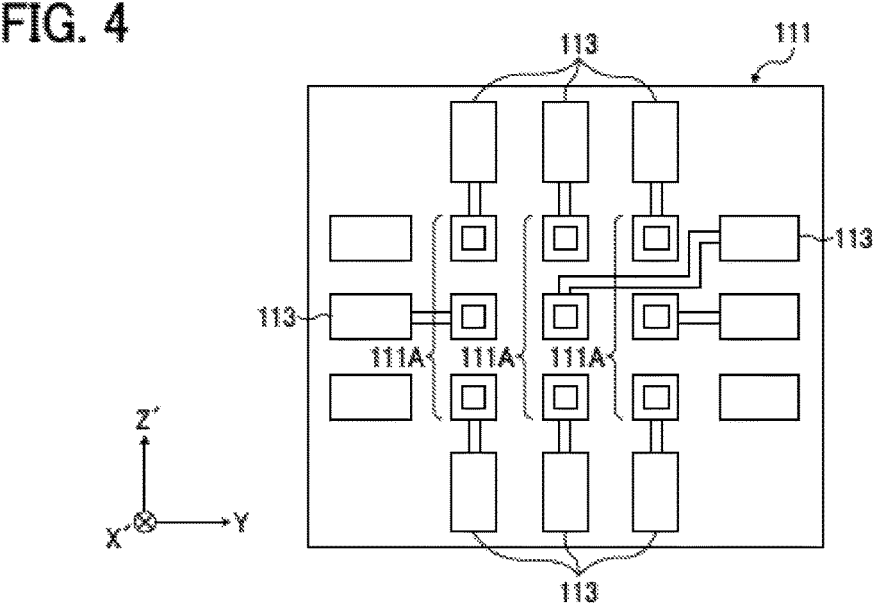
FIG. 4 is a diagram illustrating the configuration of a light source unit according to the first embodiment of the present invention.

FIG. 4 is a diagram illustrating the configuration of the light source unit 111 according to the present embodiment.

In the present embodiment, the light source 116 is a vertical cavity-surface emitting laser (VCSEL) array, and includes a plurality of light-emitting units 111A formed on the same (single) substrate, as illustrated in FIG. 4. The nine light-emitting units 111A are two-dimensionally disposed on the same substrate of the light source 116 as illustrated in FIG. 4, and an electrode pad 113 is connected to each of the light-emitting units 111A. When the light source 116 has the multiple light-emitting unit 111A as in the VCSEL array, the variations can be reduced in the output of a sensor due to the unique speckle pattern caused when an object such as the sheet P that causes diffuse reflection is irradiated with a semiconductor laser beam with long coherence length. As described above, in the present embodiment, cases in which the light source 116 of the light source unit 111 includes a VCSEL array having nine light-emitting units 111A are described. However, no limitation is intended thereby.

Figure 5:
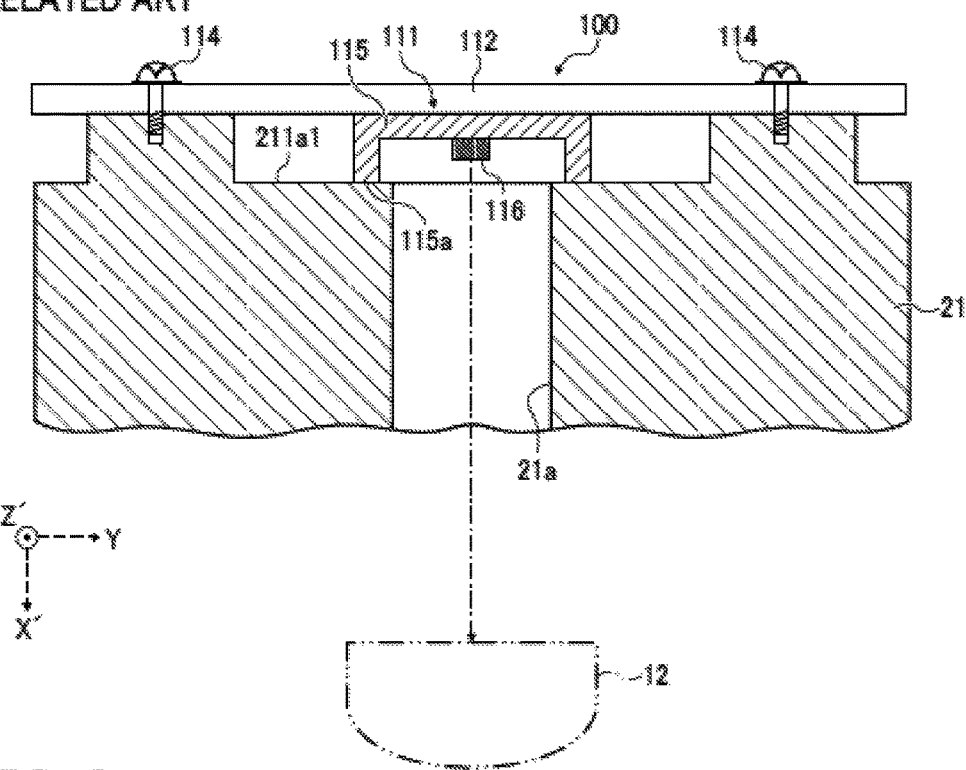
FIG. 5 is a diagram illustrating a commonly-adopted immobile structure of an irradiation system and a housing.

FIG. 5 is a diagram illustrating a commonly-adopted immobile structure of the irradiation system 100 and the housing 21. In the commonly-used irradiation system 100, as illustrated in FIG. 5, in order to improve the precision of the distance between the light source unit 111 and the collimator lens 12, the position of the light source unit 111 is aligned by making the light source 111 contacts a part of the housing 21 where the opening hole 21a opens (note that such a part of the housing 21 exists in the X'-axis direction the present embodiment, and is referred to as a base 211a1).

Figure 6:
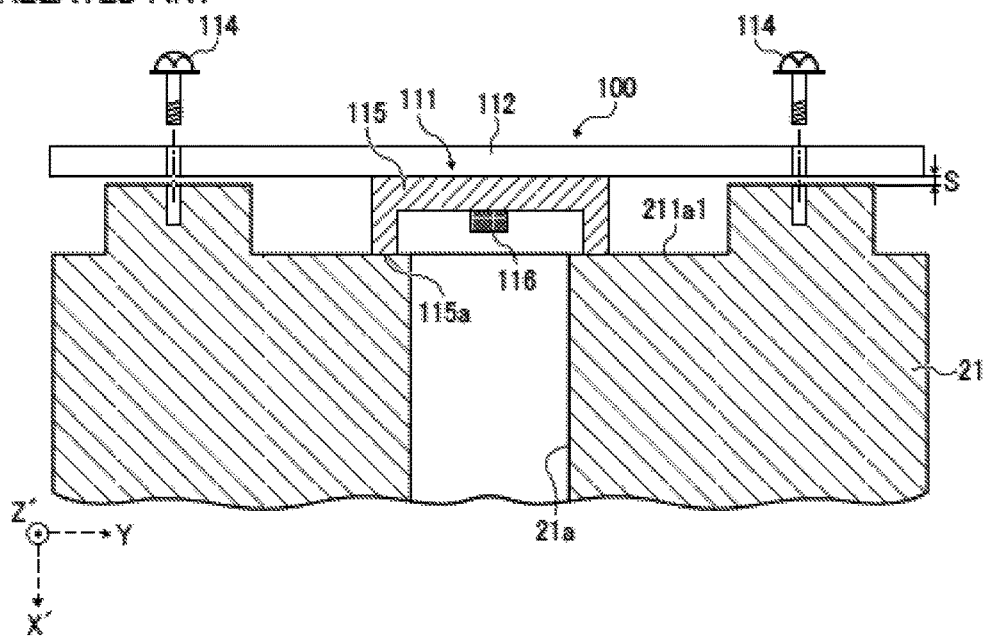
FIG. 6 is a diagram illustrating a defective condition of the immobile structure illustrated in FIG. 5.

FIG. 6 is a diagram illustrating a defective condition of the immobile structure illustrated in FIG. 5. However, in such an attachment method, as illustrated in FIG. 6, there may be a gap S caused between the housing 21 and the circuit board 112 in the range of the tolerance of the heights of the housing 21 or the light source unit 111.

Figure 7:
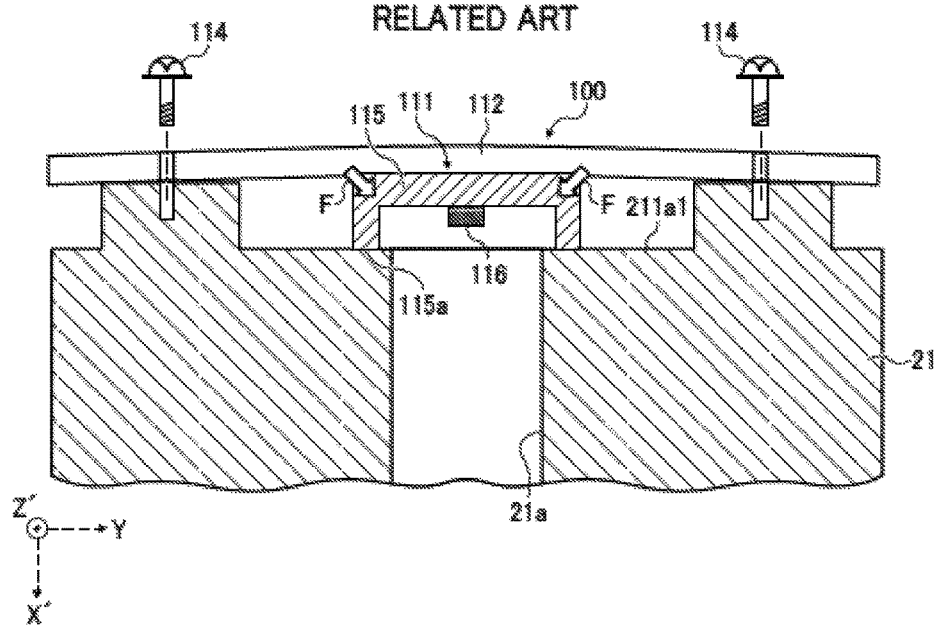
FIG. 7 is another diagram illustrating a defective condition of the immobile structure illustrated in FIG. 5.

FIG. 7 is another diagram illustrating a defective condition of the immobile structure illustrated in FIG. 5. If the light source unit 111 is attached to the housing 21 in a state where the gap P is being caused, as illustrated in FIG. 7, the light source unit 111 is sandwiched by the base 211a1 and the circuit board 112, and the compressive stress F is applied to the light source unit 111 from the circuit board 112 where the light source unit 111 serves as the fulcrum. When such a compressive stress F is applied, the polarization ratio changes, and the discrimination accuracy may deteriorate. Note that such a compressive stress F is caused not only in the cases where the light source unit 111 and the circuit board 112 are separately configured, but also in the cases where the light source unit 111 and the circuit board 112 are formed as a single integrated light source unit. As described above, in commonly-used optical sensors, the changes in the polarization caused due to the reflection on the sheet P is a parameter a commonly-used optical sensor for discrimination. However, in order to achieve specialized discrimination such as the discrimination of brands, as described above, the individual difference in the polarization of the light source unit 111 needs to be taken into consideration, and such an individual difference is to be reduced.

In the present embodiment, as illustrated in FIG. 3, the irradiation system 100 is fixed to the housing 21 by a fastening member 114 such as a screw, via the circuit board 112. The light source unit 111 is disposed on the circuit board 112 so as to protrude in the light emitting direction of the light source unit 111 (X'-axis direction). When the irradiation system 100 is attached to the housing 21, the light source unit 111 is disposed at a portion of the circuit board 112 such that the circuit board 112 of the irradiation system 100 contacts the housing 21 and the light source unit 111 does not contact the housing 21. In other words, in the optical sensor 2245, the housing 21 holds the irradiation system 100, the first light detection system 102, and the second light detection system 101, and the light source unit 111 is attached to the housing 21 via the circuit board 112 with no direct contact between the light source unit 111 and the housing 21. Accordingly, when the light source unit 111 is attached to the housing 21, the direct application of the compressive stress to the light source unit 111 is prevented, and the chances of the changes in the polarization ratio of the light source unit 111 can be reduced.

The housing 21 contacts the circuit board 112 only at the portions around a fixed-by-fastening portion 213 between the circuit board 112 and the housing 21, and has a structure where the contacting area is small but the stable support is not affected. In other words, in the present embodiment, the light source unit 111 is configured such that the light source unit 111 is not sandwiched by the housing 21 and the compressive stress F is not applied to the light source unit 111 due to an error in the shape of the housing 21, in order to avoid the changes in the polarization ratio of the light source unit 111. In other words, a plurality of bosses 210 that fix the light source unit 111 and a concave portion 211 that accommodates the light source unit 111 are formed by the housing 21. The concave portion 211 becomes hollow towards the light emitting direction of the light source unit 111 (X'-axis direction). On the base 211a of the concave portion 211, the opening hole 21a is made. The space S1 between the base 211a and a mounting plane 210a of the boss 210 on which the circuit board 112 is fixed is made wider than the height (amount of protrusion) S2 between the plane 111b on which the light source unit 111 is mounted and the plane 111a located in the light emitting direction (X'-axis direction) of the light source unit 111. Accordingly, when the circuit board 112 on which the light source unit 111 is mounted is fixed to the mounting plane 210a of the boss 210, the space S1a is formed between the plane 111a of the light source unit 111 and the base 211a of the housing 21. In other words, the light source unit 111 is fixed to the housing 21 that supports the irradiation system 100, the polarizing filter 16, and the photoreceptor 17 in the light emitting direction of the light source unit 111 (X'-axis direction), via the space S1a in the light emitting direction (X'-axis direction), so as not to be sandwiched by the housing 21.

Figure 24:
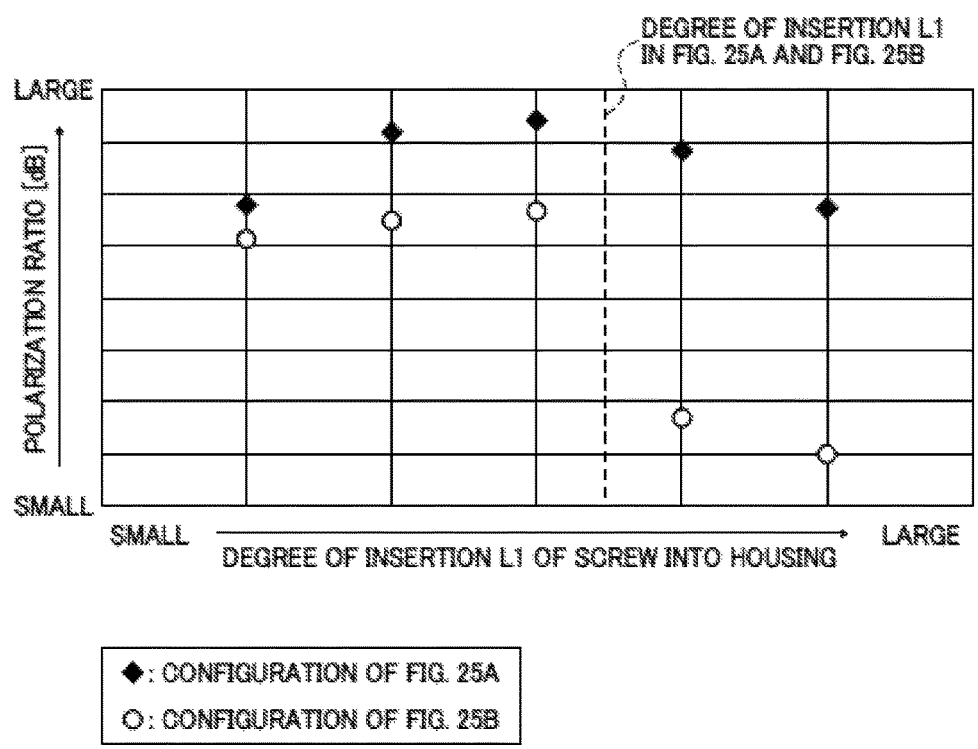
FIG. 24 depicts the results of the measurement of the polarization ratio of the light emitted from a light source unit.

FIG. 24 depicts the results of the measurement of the polarization ratio of the light emitted from the light source unit 111.

Figure 25A:
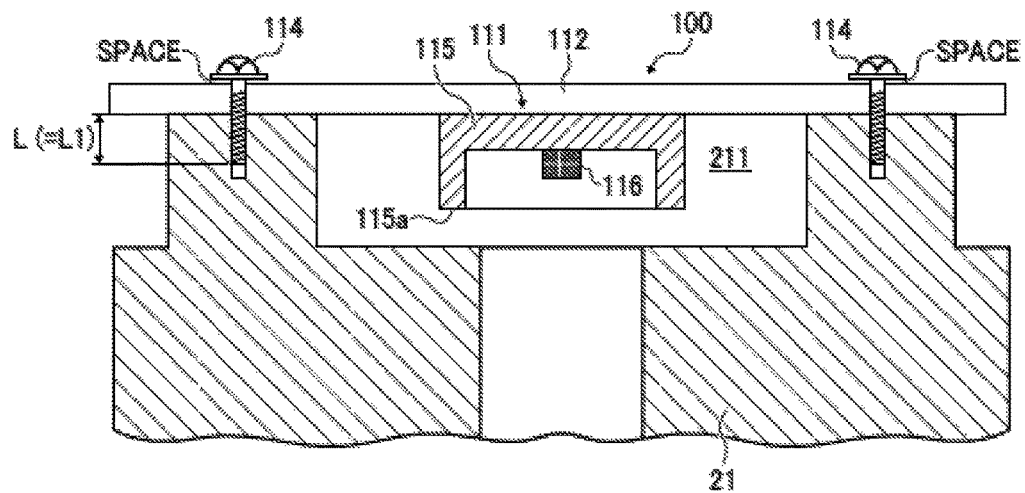
FIG. 25A and FIG. 25B are diagrams illustrating the degree of insertion of screws in the state of "L=L1" as depicted in FIG. 24.
Figure 25B:
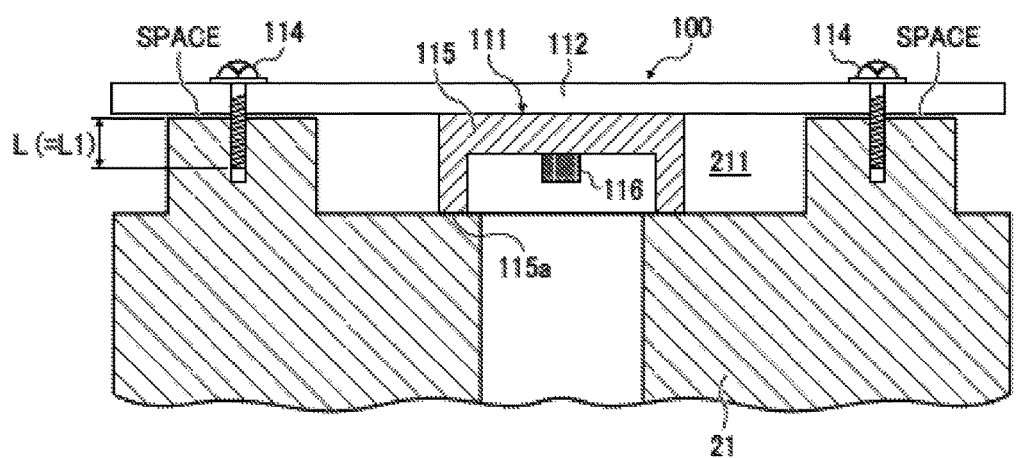

FIG. 25A and FIG. 25B are diagrams illustrating the degree of insertion of the screws 114 in the state of "L=L1" as depicted in FIG. 24.

Figure 26A:
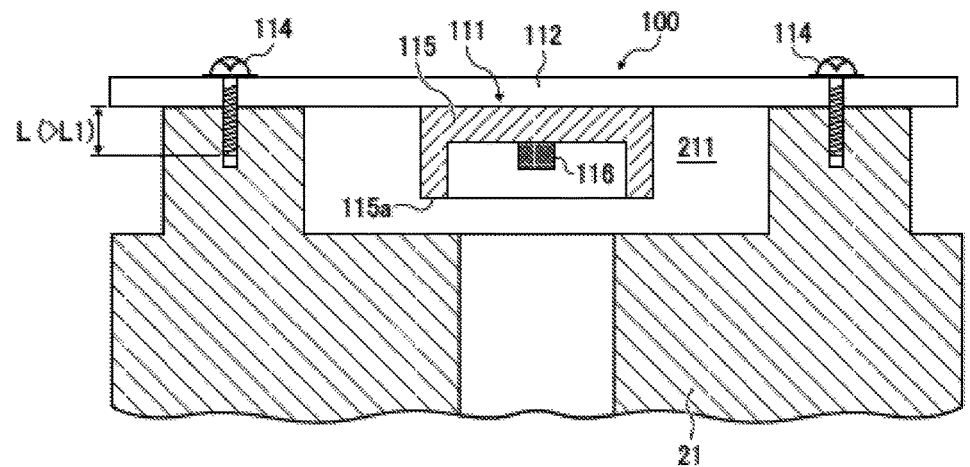
FIG. 26A and FIG. 26B are diagrams illustrating the degree of insertion of screws in the state of "L>L1" as depicted in FIG. 24.
Figure 26B:
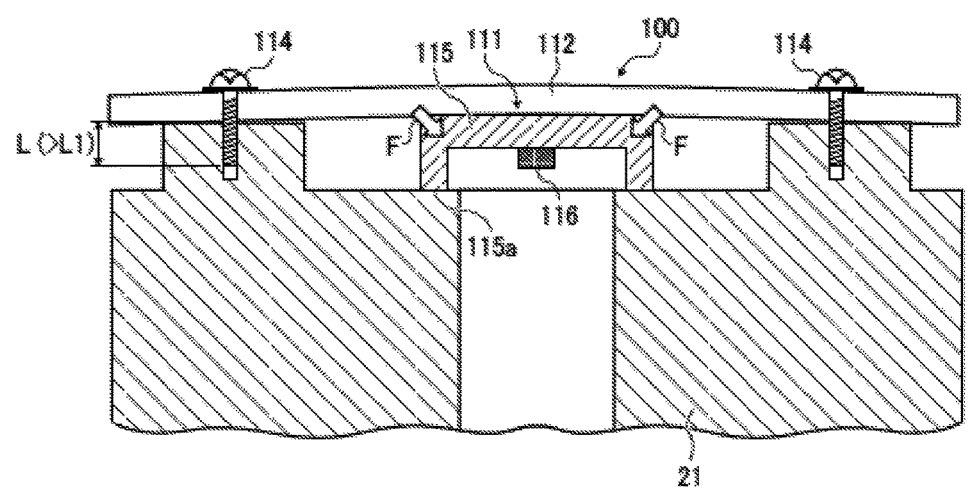

The changes in the polarization ratio of the light emitted from the light source unit 111 in the process of fastening the screws 114 are measured using the configuration as illustrated in FIG. 25A in which the circuit board 112 on which the package 115 is mounted contacts the housing 21 but the end surface 115a of the package 115 does not contact the housing 21 as well as the configuration as illustrated in FIG. 25B in which the end surface 115a of the package 115 of the light source unit 111 contacts the housing 21. The results of this measurement is depicted in FIG. 24. The compressive stress that is applied to the light source 116 is varied by the number of revolutions (degree of insertion L) of the fastening screws 114. According to the results depicted in FIG. 24, it is determined that the polarization ratio changes widely only in the configuration illustrated in FIG. 25B in which the end surface 115a of the package 115 contacts the housing 21. In FIG. 24, the polarization ratio changes widely at a screw position where the compressive stress is caused to the package 115 (position where the circuit board 112 start being bent). Note that FIG. 25A, FIG. 25B, FIG. 26A, and FIG. 26B are diagrams illustrating the degree of insertion L of the screws in the two configurations as described above. FIG. 25A and FIG. 25B illustrate the degree of insertion of the screws in the state of "L=L1" as depicted in FIG. 24, and FIG. 26A and FIG. 26B illustrate the degree of insertion of the screws in the state of "L>L1" as depicted in FIG. 24.

Accordingly, the light source unit 111 is not pressed against the base 211a, and free from the compressive stress F. Moreover, the direct compressive stress F onto the light source unit 111 (irradiation system 100) is eliminated, and the individual variations in the polarization ratio of the optical sensor 2245 can be reduced. As an alternative configuration of a light source unit, the light source unit 111 and the circuit board 112 may be formed as a single integrated unit. Also in such an alternative configuration, the light source unit 111 is fixed to the housing 21 via the space S1a in the light emitting direction (X'-axis direction) of the light source unit 111 without being pressed against the base 211a of the housing 21, so as not to be sandwiched by the housing 21 in the light emitting direction of the light source unit 111 (X'-axis direction). Accordingly, the compressive stress F is eliminated, and the individual variations in the polarization ratio of the optical sensor can be reduced.

Here, in the configuration in which the end surface 115a of the package 115 contacts the housing 21, compressive stress is applied by the fastening of screws in a similar manner to the measurement as described above with reference to FIG. 24, and reflected light is measured using a plurality of kinds of the sheet P. In this measurement, it is assumed that the sheet P is measured at the same point.

Figure 27A:
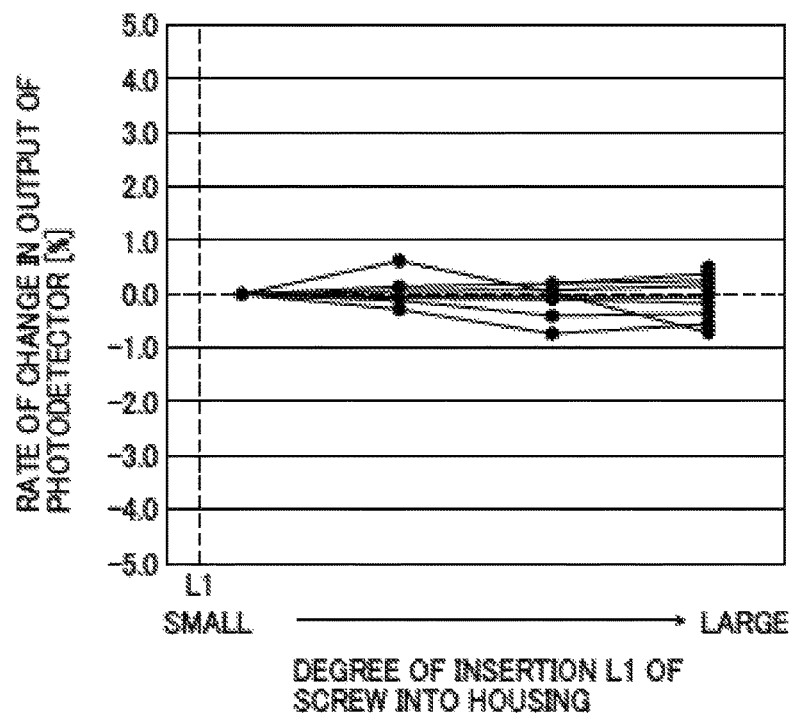
FIG. 27A and FIG. 27B depict the changes in the output of a first photodetector and a second photodetector when measurement is performed, according to the first embodiment of the present invention.
Figure 27B:
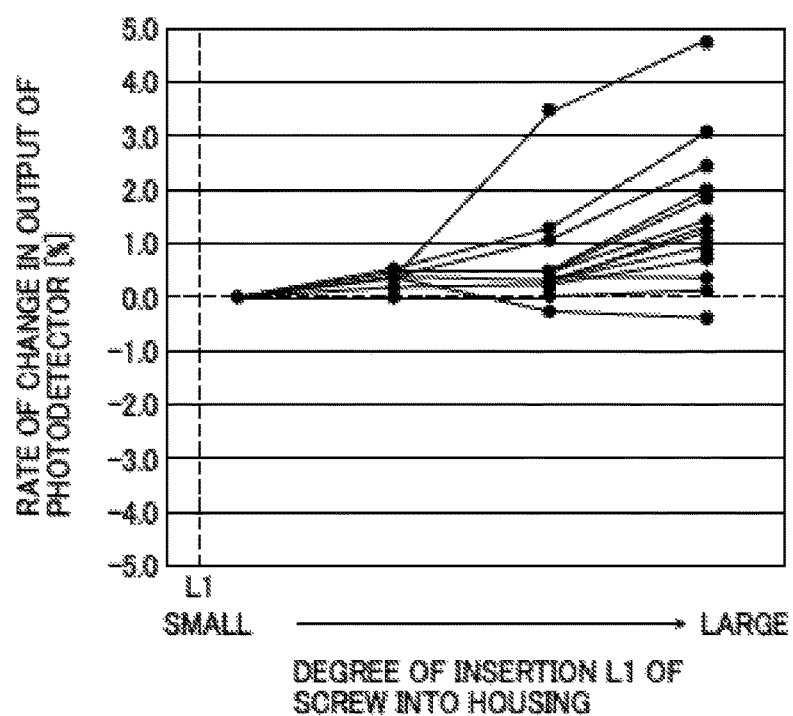

FIG. 27A and FIG. 27B depict the changes in the output of a first photodetector and a second photodetector when measurement is performed, according to the first embodiment.

Figure 8:
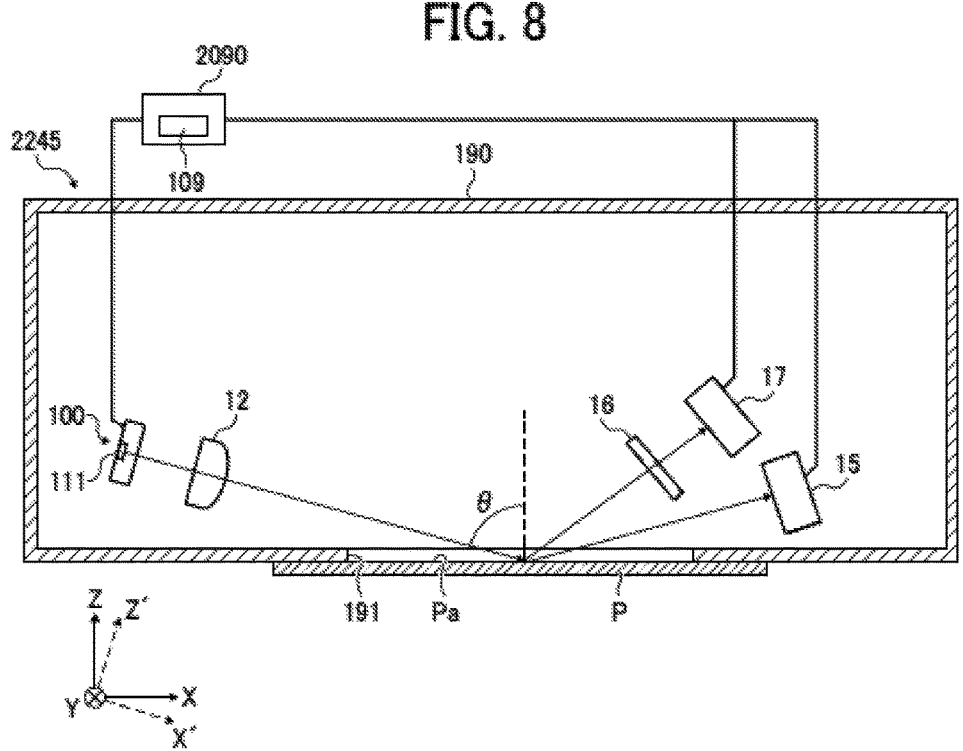
FIG. 8 is a diagram illustrating the incident angle of the light that enters a recording medium, according to the first embodiment of the present invention.

Here, the first photodetector is a detector that detects specular reflection, and the second photodetector is a detector that includes a polarizing filter and detects the changed components in the polarized light. FIG. 27A indicates the rate of change in the output of the first photodetector, and FIG. 27B indicates the rate of change in the output of the second photodetector. The measurement in FIG. 27A and FIG. 27B is performed with the configuration as illustrated in FIG. 8.

The line segments depicted in FIG. 27A and FIG. 27B indicate the results of the measurement obtained from several brands of sheet. At the photodetector (second photodetector) that detects changes in polarization, as depicted in FIG. 27B, the influence of the changes in the polarization ratio caused due to compressive stress is significant. It varies according to the brand of sheet, but in this experiment, the changes of approximately 0 to 5 percent are observed. On the other hand, at the photodetector (first photodetector) that detects specular reflection, as depicted in FIG. 27A, not much change is observed. Accordingly, among the reflections on the sheet P, it is considered that the detection of polarized light is particularly sensitive to the compressive stress onto the light source 116.

In other words, the output of the second photodetector varies, and in the strict discrimination of an object, in particular, in the discrimination of the brand of the sheet, some brands having similar reflective properties could erroneously be discriminated. In view of the above circumstances, it is configured in the present embodiment such that the end surface 115a of the package 115 does not contact the housing 21 and the circuit board 112 on which the package 115 is mounted contacts the housing 21. Accordingly, the variations in the polarization ratio of each of the optical sensors are reduced.

For these reasons, in the present embodiment, an optical sensor checks the obtained values against the values of the database prepared in advance when the optical sensor discriminates the brand of the sheet. The database consists of the outputs of the photodetectors of a standard optical sensor. However, if the degree of insertion L of the screws becomes error factor and the outputs of the second photodetector vary for each of the optical sensors due to the degree of insertion L of the screws, the brand of the sheet may erroneously be discriminated.

Figure 28:
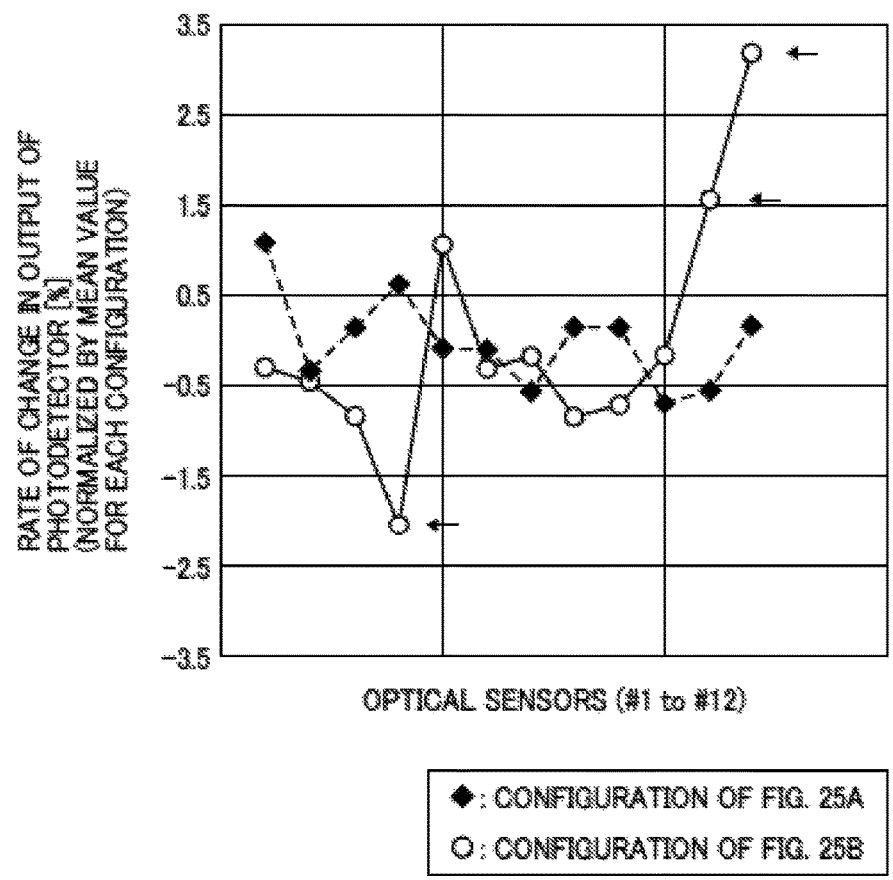
FIG. 28 is a graph indicating the measurement results of the variations in the outputs of the second photodetectors of optical sensors that are assembled with the same fastening condition of screws.

FIG. 28 is a graph indicating the measurement results of the variations in the outputs of the second photodetectors of twelve optical sensors that are assembled with the same fastening condition of screws.

In this measurement, the same point of the same sheet is measured, and the values that are normalized by the mean value of the twelve optical sensors are plotted for each configuration. As described above, it is configured in the present embodiment such that the package 115 does not contact the housing 21, and the variations in the output of the second photodetector (individual difference among sensors) can be reduced. For this reason, the brand of the sheet can be discriminated in a stable manner according to the present embodiment.

A method of fixing the light source unit 111 (irradiation system 100) is not limited to the fixation by fastening using the fastening member 114, but may be a fixation by bonding using, for example, ultraviolet (UV)-curable resin. In such cases, the circuit board 112 is bonded onto the bosses 210 for fixation. Note that in FIG. 3, the reference sign "A" indicates the pitch of the fixation of the fixed-by-fastening portion 213 implemented by the fastening member 114.

Figure 9:
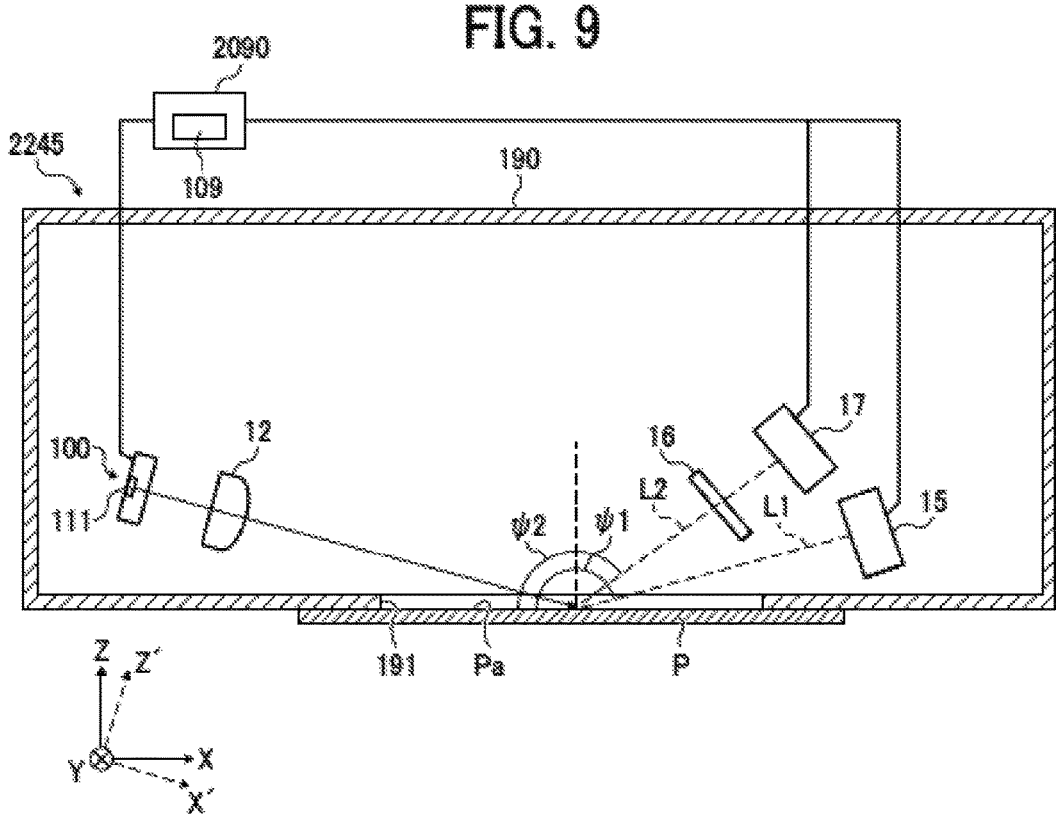
FIG. 9 is a diagram illustrating the layout of first and second photodetectors according to the first embodiment of the present invention.

As illustrated in FIG. 8, the irradiation system 100 is disposed such that the S-polarized linear light is emitted to the sheet P by the light source unit 111. The collimator lens 12 is disposed on the optical path (21a) of the light emitted from the light source unit 111, and approximately collimates the light. The light that has passed through the collimator lens 12 passes through the opening 191 formed on the dark box 190 to illuminate the surface Pa of the sheet P that faces the opening 191. In FIG. 8, the incident angle θ of the light emitted from the light source unit 111 (irradiation system 100) is 80 degrees on the sheet P. In the present embodiment, as illustrated in FIG. 9, the photoreceptor 15 is disposed on the +X side of the irradiation center in the X-axis direction. In this configuration, the angle $\psi 1$ which the surface Pa of the sheet P forms with a line L1, which is drawn through the irradiation center and the center of the photoreceptor 15, is 170 degrees. Note that the center of the light emission of the light source unit 111, the irradiation center, the center of the polarizing filter 16, the center of the photoreceptor 17, and the center of the photoreceptor 15 are disposed on substantially the same plane. Moreover, the angle $\psi 2$ which the surface Pa of the sheet P forms with a line L2, which is drawn through the irradiation center and the centers of the polarizing filter 16 and the photoreceptor 17, is 150 degrees. Note also that the illustration of the housing 21 is omitted in FIG. 8 and FIG. 9.

Because the center of light emission of the light source unit 111 of the irradiation system 100, the irradiation center, and the center of the photoreceptor 17 are substantially on a same plane in the present embodiment, the diffuse reflection light whose polarization direction is rotated on the surface Pa of the sheet P is not detected by the photoreceptor 17. By contrast, the multiple-diffuse reflection light whose polarization direction is rotated upon multiple reflections on the surface Pa of the sheet P as well as the internal diffusion reflection light whose polarization direction is rotated upon multiple reflections inside the sheet P are further reflected multiple times after going out of the plane in the reflection path and includes again the light reflected on the plane. Accordingly, these multiple-diffuse reflection light and internal diffusion reflection light are detected by the photoreceptor 17 that is on the same plane as the irradiation center and the center of light emission of the light source unit 111 of the irradiation system 100.

The polarizing filter 16 receives diffuse reflection light, multiple-diffuse reflection light, and internal diffusion reflection light. In the present embodiment, the polarization direction of the diffuse reflection light is same as the polarization direction of the irradiation light (S-polarized light). Accordingly, the diffuse reflection light is blocked (shielded) at the polarizing filter 16. By contrast, the polarization directions of the multiple-diffuse reflection light and the internal diffusion reflection light are rotated with reference to the polarization direction of the irradiation light. For this reason, the P-polarized components included in the multiple-diffuse reflection light and the internal diffusion reflection light pass through the polarizing filter 16. In other words, the photoreceptor 17 detects only the P-polarized components included in the multiple-diffuse reflection light and the internal diffusion reflection light.

Note that the P-polarized components included in the internal diffusion reflection light may be referred to simply as "P-polarized components of the internal diffusion reflection light". In a similar manner, the S-polarized light components included in the internal diffusion reflection light may be referred to simply as "S-polarized light components of the internal diffusion reflection light". It has been determined that the amount of the internal diffusion reflection light correlates with the thickness or density of sheet P. This is because the amount of the internal diffusion reflection light depends on the length of the path where the light passes through the fibers of the sheet P.

Figure 10:
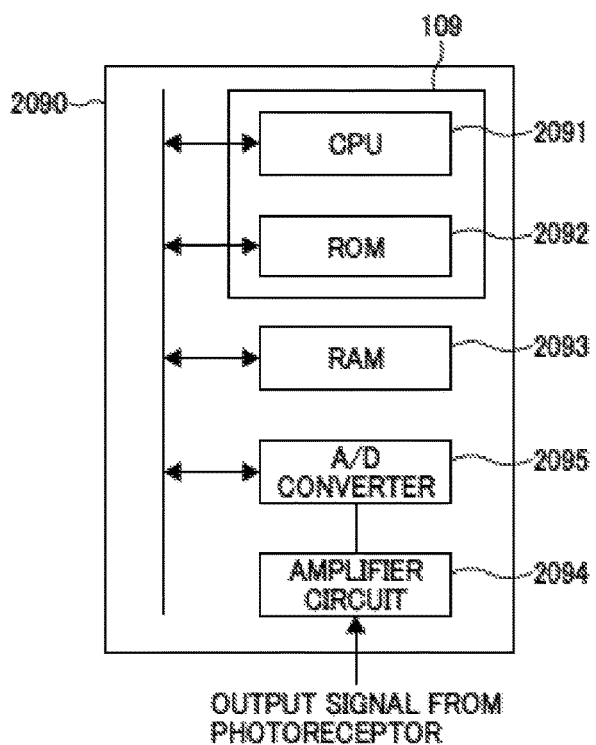
FIG. 10 is a block diagram of the configuration of a control system according to the first embodiment of the present invention.

Next, the configuration of the control circuit 2090 is described. As illustrated in FIG. 10, the control circuit 2090 includes, for example, a central processing unit (CPU) 2091, a read-only memory (ROM) 2092 in which a program described by CPU-readable codes and various kinds of data used for executing the program are stored, a random access memory (RAM) 2093 that serves as a working memory, an amplifier circuit 2094, and an analog-to-digital (A/D) converter 2095 that converts an analog signal to a digital signal. The control circuit 2090 controls the elements of the color printer 2000 under instructions from the host device 3000 as illustrated in FIG. 1, and transfers the image data sent from the host device 3000 to the optical scanner 2010 to control the image-forming operation.

The control circuit 2090 includes the processor 109 that specifies the brand of the sheet P that serves as a recording medium according to the signal level of the signal output from the optical sensor 2245. The processor 109 is mainly composed of the CPU 2091 and the ROM 2092. Each of the photoreceptor 15 and the photoreceptor 17 outputs an electrical signal (photoelectrically-converted signal) to the processor 109 according to the amount of the received light. Note that the value that is output to the processor 109 may be based, for example, on the average of the electrical signals obtained during a fixed duration in time (hereinafter, such time will be referred to as sampling time).

In the present embodiment, the sheet P is irradiated with a bundle of rays of light emitted from the irradiation system 100. In that configuration, the signal levels of the signals output from the photoreceptor 15 and the photoreceptor 17 are referred to as "S01" and "S02", respectively.

The control circuit 2090 provided with the processor 109 estimates (specifies) the brand of the sheet P based on the signals "S01" and "S02" output from the photoreceptor 15 and the photoreceptor 17, respectively, when the sheet P is irradiated with a bundle of rays of light emitted from the irradiation system 100. In the present embodiment, the values of S01 and S02 of the sheet P of varying brands compatible with the color printer 2000 are measured for each of the brands of the sheet P and the results are stored in the ROM 2092 of the control circuit 2090 as a "sheet P discrimination table", in advance of shipment, for example, when adjustment processes are performed in the factory.

Figure 11:
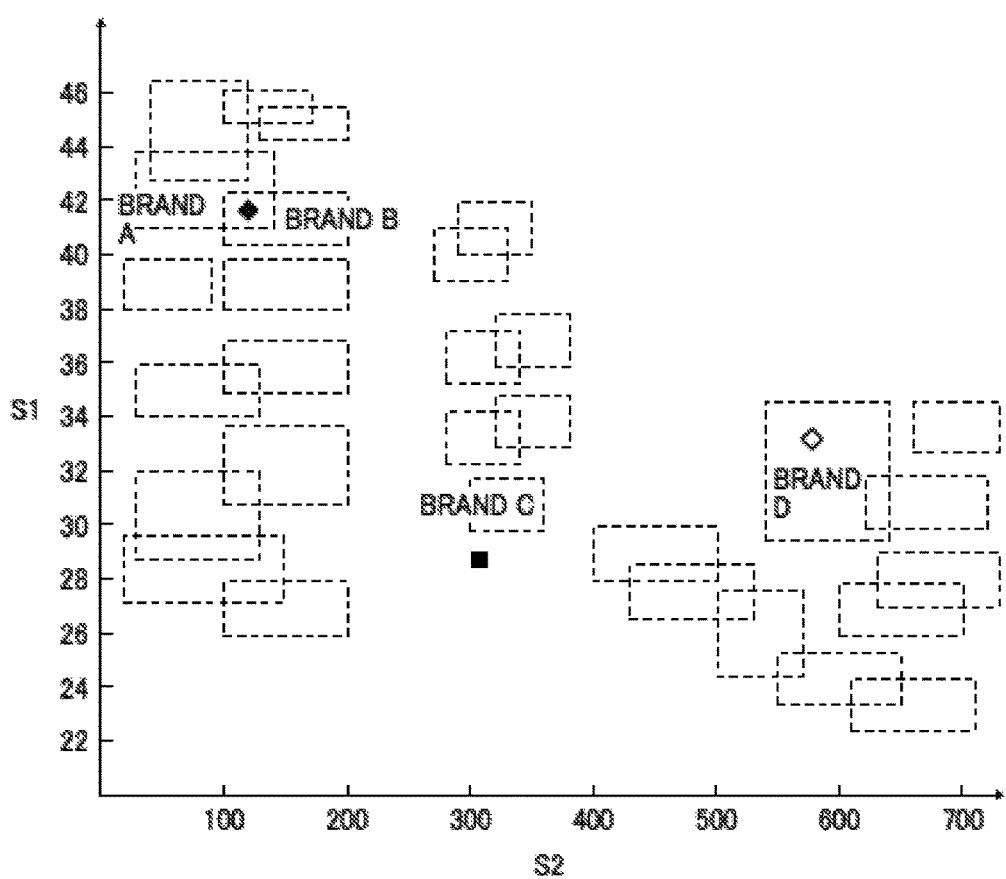
FIG. 11 is a diagram illustrating the relation of the brands of a recording medium and the signals output from the first and second photodetectors, according to the first embodiment of the present invention.

FIG. 11 is a diagram illustrating the relation of the brands of a recording medium and the signals output from the first and second photodetectors, according to the first embodiment.

More specifically, the measured values of S01 and S02 for thirty brands of sheet P, which are available in Japan, are illustrated in FIG. 11. Note that each of the rectangular frames indicated by broken lines as illustrated in FIG. 11 indicates a range of variation in the measurement of same brand. For example, when the measured values of S01 and S02 indicates the position indicated by a rhombus (see FIG. 11), the brand of the sheet P is determined to be the brand D by the processor 109. When the measured values of S01 and S02 indicates the position indicated by a filled rectangular (see FIG. 11), the brand of the sheet P is determined to be the brand C by the processor 109 as the region of the brand C is closest to the position of the filled rectangular. When the measured values of S01 and S02 indicates the position indicated by a filled rhombus (see FIG. 11), the brand of the sheet P is estimated to be the brand A or the brand B by the processor 109. In this case, for example, the difference between the average of the values obtained for the Brand A and the measurement value as well as the difference between the average of the values obtained for the Brand B and the measurement value are computed by the control circuit 2090. Then, the processor 109 determines the brand of the sheet P to be either of the brands where the resultant difference is smaller than the other. Alternatively, the brand of the sheet P may be determined as follows. Firstly, it is assumed that the brand of the sheet P is the Brand A, and the variation of the Brand A is calculated again by the control circuit 2090 with the data to which the measurement value is added. Secondly, it is assumed that the brand of the sheet P is the Brand B, and the variation of the Brand B is calculated again by the control circuit 2090 with the data to which the measurement value is added. Then, the processor 109 selects the brand of the sheet P to be the brand where recalculated variation is smaller than the other.

Figure 12:
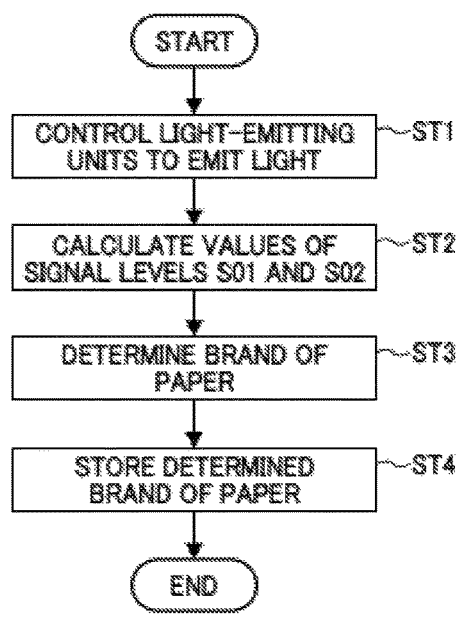
FIG. 12 is a flowchart depicting an example of the paper-type discrimination processes using the optical sensor according to the first embodiment of the present invention.

FIG. 12 is a flowchart depicting an example of the paper-type discrimination processes using the optical sensor 2245 according to the first embodiment of the present invention. When, for example, the power of the color printer 2000 is turned on and the sheet P is fed to the sheet feeding tray 2060, the control circuit 2090 performs paper-type discrimination processes using the processor 109 and the signals output from the optical sensor 2245. The paper-type discrimination processes that are performed by the control circuit 2090 according to the present embodiment are described below with reference to the flowchart of FIG. 12. In the paper-type discrimination process using the optical sensor 2245, the processor 109 of the control circuit 2090 controls the multiple light-emitting units 111A of the optical sensor 2245 to emit light in the step ST1 of FIG. 12. In the step ST2 of the paper-type discrimination process, the values of signal levels S01 and S02 are calculated from the output signals of the photoreceptor 15 and the photoreceptor 17. In the step ST3 of the paper-type discrimination process, a sheet-type discrimination table that is stored in the ROM 2092 is referred to, and the brand of the sheet P is determined from the obtained values of S1 and S2. In the step ST4 of the paper-type discrimination process, the determined brand of the sheet P is stored in the RAM 2093, and the paper-type discrimination process is terminated. In other words, the processor 109 (control circuit 2090) according to the first embodiment discriminates the sheet P based on the signal levels of the signals output from the photoreceptor 17 and the photoreceptor 15, which serve as the first and second photodetectors, respectively.

The control circuit 2090 reads the sheet P from the RAM 2093 when a request for a print job is received, and then determines optimal development conditions and transfer conditions, which are examples of the image-forming conditions, from the development and transfer table stored in the ROM 2092 for the specified brand of the sheet P. Then, in the cases of color printing, the control circuit 2090 controls the developing device and transfer device of the image station of each color in accordance with the determined optimal development conditions and transfer conditions. For example, the printer controller 2090 controls the transfer voltage or the amount of toner. Accordingly, a high-quality image is formed on the sheet P. In other words, the color printer 2000 includes the control circuit 2090 that serves as an adjuster that adjusts the image-forming conditions based on the sheet P as an object specified by the recording medium discrimination device 300. Moreover, the control circuit 2090 that serves as an adjuster has the function of determining the brand of the sheet P according to the signal level of the signal output from the optical sensor 2245 and adjusting the image-forming condition according to the determined brand of the sheet P.

Second Embodiment

Figure 13:
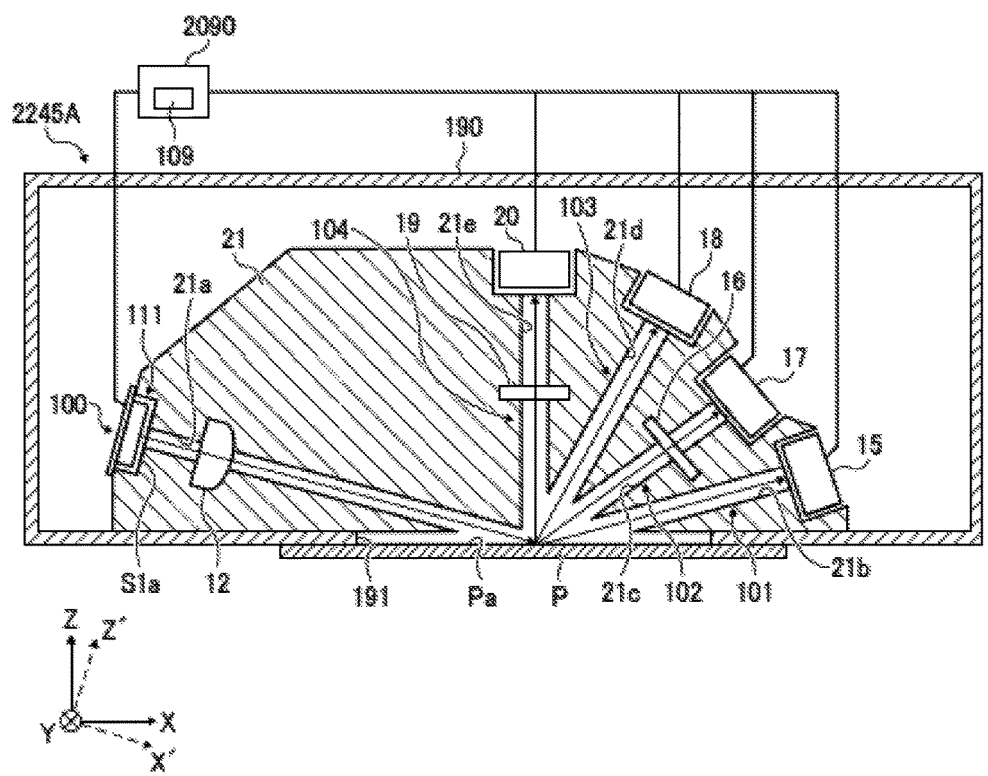
FIG. 13 is a magnified view of the configuration of an optical sensor according to a second embodiment of the present invention.

FIG. 13 is a magnified view of the configuration of an optical sensor 2245A according to a second embodiment of the present invention. Due to disturbance light or stray light, an error may occur in the paper-type discrimination. In order to avoid such situation, as illustrated in FIG. 13, the number of light detection systems is increased compared with the configuration according to the first embodiment. In addition to the two photoreceptors 15 and 17, the optical sensor 2245A as illustrated in FIG. 13 further includes a third light detection system 103 and a fourth light detection system 104. The third light detection system 103 includes a photoreceptor 18 that serves as a third photodetector. The fourth light detection system 104 includes a polarizing filter 19 that serves as a polarizing optical element, and a photoreceptor 20 that serves as a fourth photodetector. In other words, the optical sensor 2245A according to the second embodiment includes the first to fourth light detection systems 101 to 104.

In the housing 21 of the optical sensor 2245A, the opening holes 21a to 21c and opening holes 21d and 21e are formed. The opening hole 21d is the path through which the light reflected on the surface Pa of the sheet P (on the incident plane of the sheet P) by diffuse reflection passes through, and the opening hole 21e is the path through which the light reflected on the surface Pa of the sheet P (on the incident plane of the sheet P) by diffuse reflection passes through. The photoreceptor 18 is disposed on the optical path (opening hole 21d) of the light reflected on the surface Pa of the sheet P (on the incident plane of the sheet P) by diffuse reflection. The photoreceptor 18 is disposed at a position so as to receive the surface diffuse reflection light, the multiple-diffuse reflection light, and the internal diffusion reflection light.

The polarizing filter 19 is disposed on the optical path (opening hole 21e) of the light reflected on the surface Pa of the sheet P (on the incident plane of the sheet P) by diffuse reflection, and the photoreceptor 20 is disposed on the same optical path (opening hole 21e) to receive the light separated by the polarizing filter 19. In a similar manner to the polarizing filter 16, the polarizing filter 19 is oriented to transmit the P-polarized light. The photoreceptor 20 is disposed at a position so as to receive the multiple-diffuse reflection light and the internal diffusion reflection light.

Figure 14:
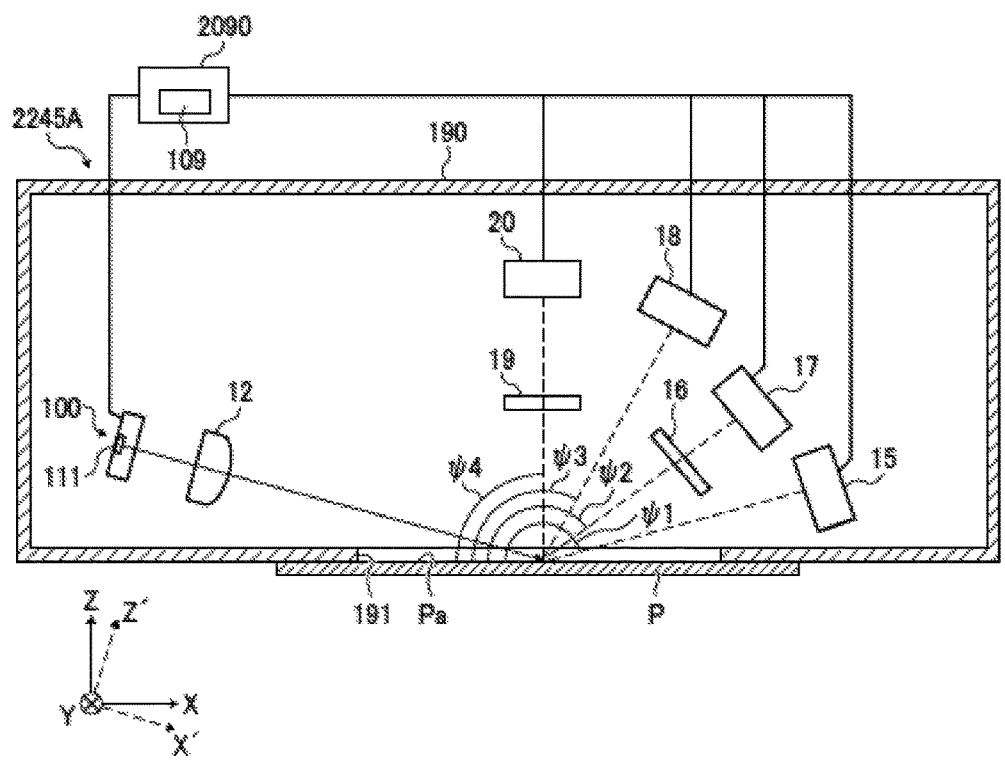
FIG. 14 is a diagram illustrating the layout of first to fourth photodetectors according to the second embodiment of the present invention.

FIG. 14 is a diagram illustrating the layout of first to fourth photodetectors according to the second embodiment of the present invention. In the optical sensor 2245A the present embodiment, the center of the light emission of the light source unit 111 of the irradiation system 100, the irradiation center, the center of the polarizing filter 19, the center of the photoreceptor 18, and the center of the photoreceptor 20 are disposed on substantially the same plane. As illustrated in FIG. 14, the angle ψ3 which the surface Pa of the sheet P forms with a line L3, which is drawn through the irradiation center and the center of the photoreceptor 18, is 120 degrees. Moreover, the angle ψ4 which the surface Pa of the sheet P forms with a line L4, which is drawn through the irradiation center and the center of the photoreceptor 20, is 90 degrees.

Next, the paper-type discrimination processes using the processor 109 of the control circuit 2090 and the signals output from the optical sensor 2245A are described below. In the present embodiment, when the sheet P is irradiated with the light emitted from the irradiation system 100, the signal levels of the signals output from the photoreceptors are amplified by the amplifier circuit 2094 of the control circuit 2090 as illustrated in FIG. 10. In that configuration, the signal levels of the signals output from the photoreceptor 18 and the photoreceptor 20 are referred to as "S03" and "S04", respectively. In the present embodiment, in order to make the signal levels of the S03 and S04 become approximately equivalent to that of the S02, the photoreceptor 18 and the photoreceptor 20 are disposed at positions closer to the irradiation center than the photoreceptor 17, and the taking-in angle of the reflected light is increased to a larger angle than the taking-in angle of the reflected light at the photoreceptor 17. Note that it is not always necessary to make the signal levels of the output of all the light detection systems become approximately equivalent to each other. For example, when the output signal of the photoreceptor 15, which serves as the second photodetector that detects specular reflection light, is amplified by another amplifier circuit 2094, it is satisfactory as long as the signal levels of the output of the photoreceptors 17, 18, and 20, which serve as the first, third and fourth photodetectors, respectively, are approximately equivalent to each other. The processor 109 (control circuit 2090) according to the second embodiment discriminates the sheet P based on the signal levels of the signals output from the photoreceptors 17, 15, 18, and 20, which serve as the first, second, third, and fourth photodetectors, respectively.

Figure 15:
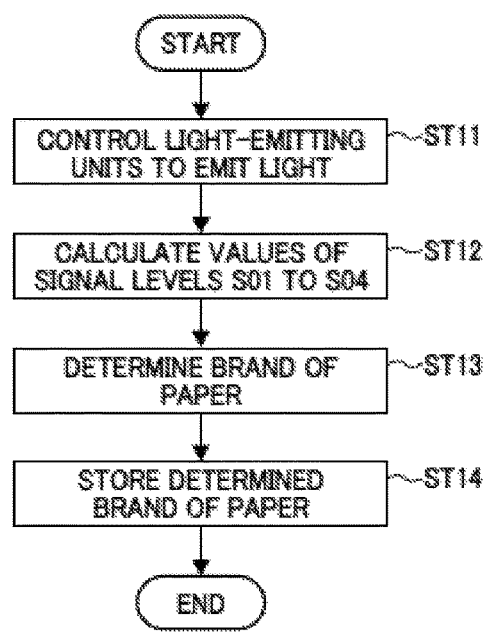
FIG. 15 is a flowchart depicting an example of the paper-type discrimination processes using the optical sensor according to the second embodiment of the present invention.

In the paper-type discrimination process using the optical sensor 2245A, the processor 109 of the control circuit 2090 controls the multiple light-emitting units 111A of the optical sensor 2245 to emit light at the same time in the step ST11 of FIG. 15. In the step ST12 of the paper-type discrimination process, the values of signal levels S01 to S04 are calculated from the output signals of the photoreceptors 15, 17, 18, and 20. In the step ST13 of the paper-type discrimination process, the sheet-type discrimination table stored in the ROM 2092 is referred to, and the brand of the sheet P is determined from the obtained values of S01, S02, S03, and S04. In the step ST14 of the paper-type discrimination process, the determined brand of the sheet P is stored in the RAM 2093, and the paper-type discrimination process is terminated. In this configuration, the values of S01, S02, S03, S04 of the sheet P of varying brands compatible with the color printer 2000 are measured for each of the brands of the sheet P and the results are stored in the ROM 2092 of the control circuit 2090 as a "sheet P discrimination table", in advance of shipment, for example, when adjustment processes are performed in the factory.

As described above, the first to fourth light detection systems 101 to 104 (photoreceptors 17, 15, 18, and 20, and polarizing filters 16 and 19) are provided to detect the light reflected to several different directions, and the sheet P is discriminated using the output levels of the signals (detection values) output from the photoreceptors 17, 15, 18, and 20. Accordingly, precise determination becomes possible in spite of the existing disturbance light or stray light.

When the first to fourth light detection systems 101 to 104 are provided, the control circuit 2090 may roughly narrow down the paper type using the signal levels S01 and S02 and then determine the brands of the sheet P using the signal levels S03 and S04. As described above, a plurality of light detection systems (photoreceptors 17, 15, 18, and 20, and polarizing filters 16 and 19) are provided to detect the light reflected to several different directions, and the sheet P is discriminated using the output levels of the signals output from the photoreceptors 17, 15, 18, and 20. Accordingly, precise determination becomes possible in spite of the existing disturbance light or stray light.

In the present embodiment, the light detection system includes the third and fourth light detection systems 103 and 104. However, the optical sensor may include three light detection systems consisting of the third light detection system 103 and the two light detection systems of the optical sensor 2245 according to the first embodiment.

Third Embodiment

Figure 16:
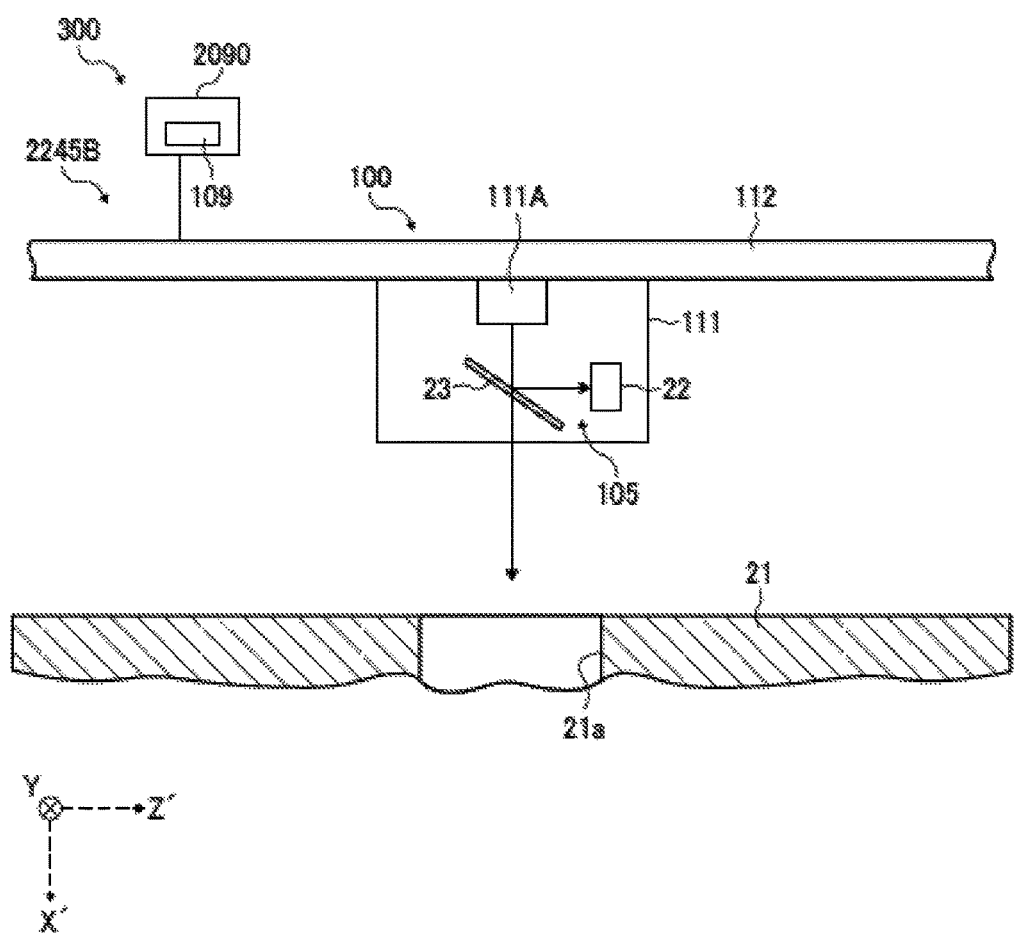
FIG. 16 is a schematic diagram of the configuration of an irradiation system of an optical sensor, according to a third embodiment of the present invention.

FIG. 16 is a schematic diagram of the configuration of an irradiation system of an optical sensor 2245B, according to a third embodiment of the present invention.

As illustrated in FIG. 16, the light source unit 111 of the optical sensor 2245B according to the present embodiment includes a fifth light detection system 105 that checks the amount of the light emission of a light-emitting unit 111A. The fifth light detection system 105 includes a beam splitter 23 as an optical element that is disposed immediately after the light-emitting unit 111A to separate a portion of the irradiation light, and a photoreceptor 22 that serves as a fifth photodetector that receives the light separated by the beam splitter 23. These photoreceptor 22 and the beam splitter 23 are installed in the light source unit 111. In the present embodiment, the signal level of the signal output from the photoreceptor 22 is referred to as "S05".

In order to check the amount of the light emission of the light-emitting unit 111A, the fifth light detection system 105 needs to be disposed prior to the opening hole 21a of the housing 21 in the optical path. This is because when the fifth light detection system 105 is disposed after the opening hole 21a of the housing 21 in the optical path, the amount of the light that is detected by the photoreceptor 22 is the amount of the laser-beam bundle that has passed through the opening hole 21a out of all the laser-beam bundles of the irradiation light, and such an amount of light is different from the amount of the light that is emitted from the light-emitting unit. In other words, in the present embodiment, the amount of irradiation light is different from the amount of the light emission of the light-emitting unit 111A.

In the present embodiment, in order to avoid variations in the polarization ratio of the irradiation light among optical sensors, the processor 109 (control circuit 2090) adjusts the amount of the light emission of the light-emitting unit 111A to an equal degree based on the signal level S05. In this configuration, the amount of the light that is emitted to the sheet P may include variations for each of the optical sensors due to the opening hole 21a as described above. For this reason, the processor 109 discriminates the brand of the sheet P according to, for example, the obtained signal levels S01/S05, S02/S05, S03/S05, and S04/S05 that are the values normalized by the amount of light emission. In other words, the processor 109 (control circuit 2090) according to the third embodiment discriminates the sheet P based on the signal levels of the signals output from the photoreceptors 17, 15, 18, 20, and 22, which serve as the first, second, third, fourth, and fifth photodetectors, respectively. In the present embodiment, the processor 109 controls the amount of the light emission of the light-emitting unit 111A to a prescribed amount according to the signal level S05 of the signal output from the photoreceptor 22.

As described above, by stabilizing the amount of the light emission of the light-emitting unit 111A, an optical sensor with a reduced polarization ratio originating from the individual variations among optical sensors can be avoided, and more accurate discrimination can be achieved.

Fourth Embodiment

Figure 17:
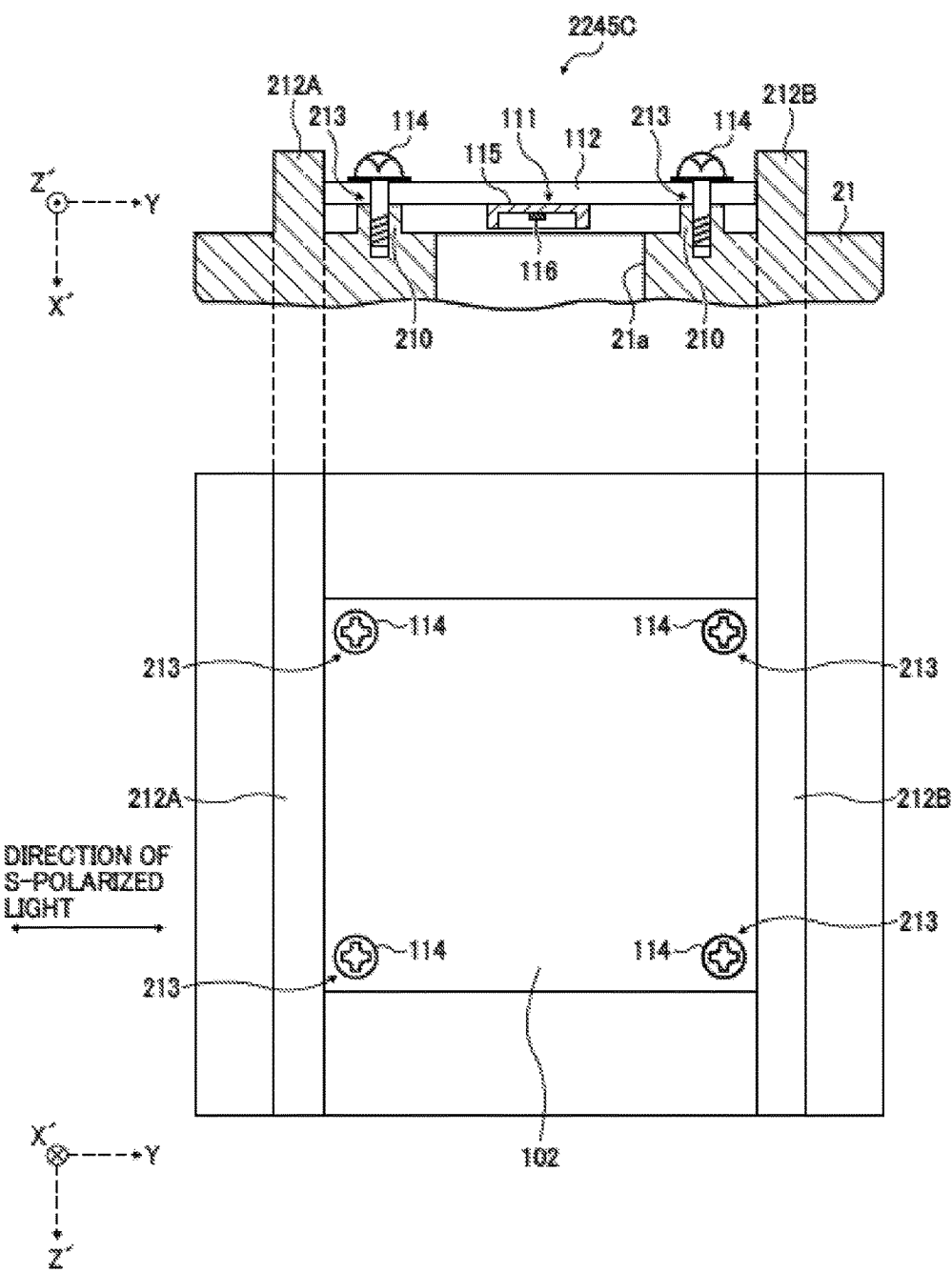
FIG. 17 is a schematic diagram of the configuration of an optical sensor, according to a fourth embodiment of the present invention.

FIG. 17 is a schematic diagram of the configuration of an optical sensor 2245C, according to a fourth embodiment of the present invention. As illustrated in FIG. 17, the housing 21 in the irradiation system 100 of the optical sensor 2245C according to the present embodiment further includes guide units 212A and 212B that restrict the rotation direction around the central axis of the X'-axis of the light source unit 111 and the circuit board 112. These guide units 212A and 212B are disposed at positions external to the fixed-by-fastening portions 213 of the circuit board 112 and the housing 21.

As described above, the guide units 212A and 212B are provided to reduce the variations in the installation position in the direction of rotation around the X'-axis that serves as the central axis. Accordingly, for the reasons described as above with reference to FIG. 22, an optical sensor with a reduced polarization ratio can be avoided, and more accurate discrimination can be achieved. In the present embodiment, the two sides of the guide units 212A and 212B that are parallel to the Z'-axis are provided for the housing 21. However, no limitation is intended thereby, and it is satisfactory as long as the direction of rotation can be restricted.

In the present embodiment, the plane 111b of the light source unit 111 existing in the light emitting direction of the light source unit 111 (X'-axis direction) is disposed in the opening 21a. In the present embodiment, the circuit board 112 is fixed to the housing 21 so as to form space between a plane of the circuit board 112 existing in the light emitting direction and the base 211a of the concave portion 211. In other words, when the light source unit 111 and the circuit board 112 are formed separately, the space existing in the light emitting direction is the space in the opening 21a, and when the light source unit 111 and the circuit board 112 are formed as a single integrated unit, the space existing in the light emitting direction is the space S1.

As described above, depending on the size of the light source unit 111 and the opening 21a, the plane 111b may be disposed in the opening 21a, and the circuit board 112 is fixed to the housing 21 such that the surface of the circuit board 112 does not contact the base 211a. Accordingly, the application of the compressive stress F is eliminated, and the individual variations in the polarization ratio of the optical sensor can be reduced.

Fifth Embodiment

Figure 18:
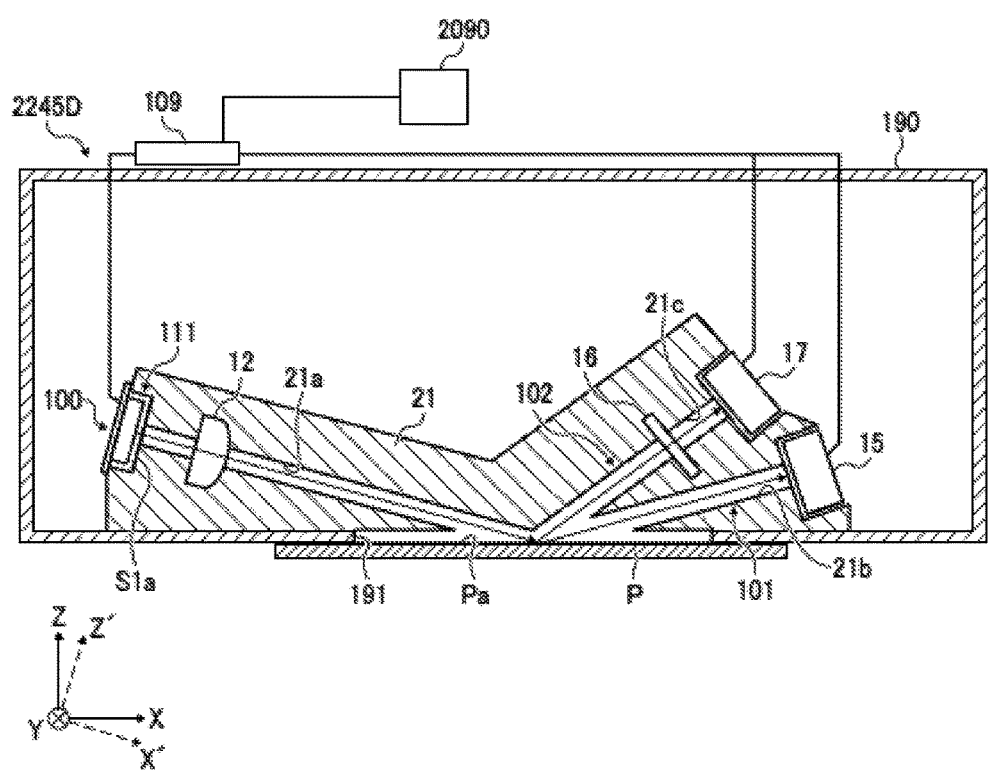
FIG. 18 is a schematic diagram of the configuration of an optical sensor, according to a fifth embodiment of the present invention.

FIG. 18 is a schematic diagram of the configuration of an optical sensor 2245D, according to a fifth embodiment of the present invention. In the first to fourth embodiments described above, the processor 109 is installed outside the optical sensors 2245 to 2245C. By contrast, the optical sensor 2245D according to the present embodiment includes the processor 109 as illustrated in FIG. 18. In this configuration, the processor 109 may be installed inside the dark box 190, but no limitation is intended thereby. When the optical sensor 2245D includes the processor 109 as described above, the processing load of the control circuit 2090 can be reduced, and the optical sensor 2245 can configure a recording medium discrimination device on its own. Note also that in the first to fifth embodiments, the housing 21 does not block the center of the optical path of the irradiation light.

The present invention is not limited to the details of the example embodiments described above, and various modifications and improvements are possible.

[First Modification]

Figure 19:
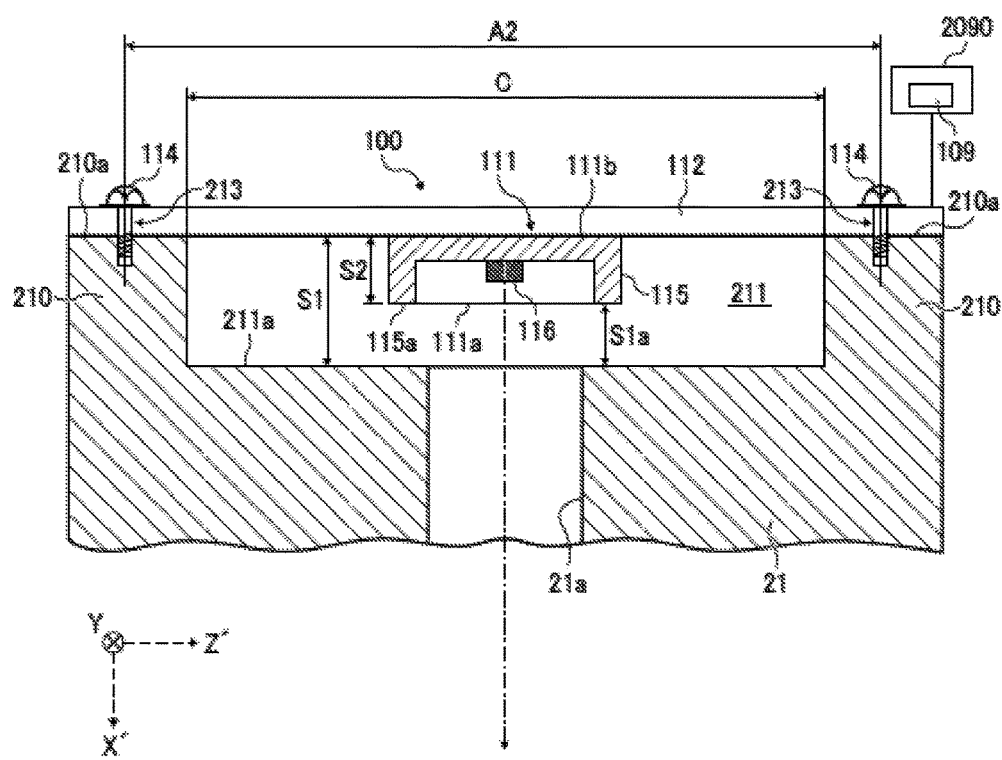
FIG. 19 is a diagram illustrating the shape of a housing in an optical sensor according to a first modification of the present invention.

FIG. 19 is a diagram illustrating the shape of a housing in an optical sensor according to a first modification of the present invention. In the first modification illustrated in FIG. 19, the irradiation system 100 is fixed to the housing 21 via the circuit board 112 at positions that are distant from the light source unit 111 but the installation is not affected. In other words, in the present embodiment, the width C of the concave portion 211, which intersect with the exit direction of the light emitted from the light source unit 111, is made wider than the first embodiment, and the pitch of the fixation of the fixed-by-fastening portion 213 implemented by the fastening member 114, which is indicated by the reference sign "A2", is made wider than the fixed pitch A1 in the first embodiment. The compressive stress F that is applied to the light source unit 111 corresponds to the moment of force that is applied for fixation. Accordingly, a reduction in the polarization ratio of the optical sensor due to the compressive stress as described above can be avoided, and more accurate discrimination can be achieved.

[Second Modification]

Figure 20:
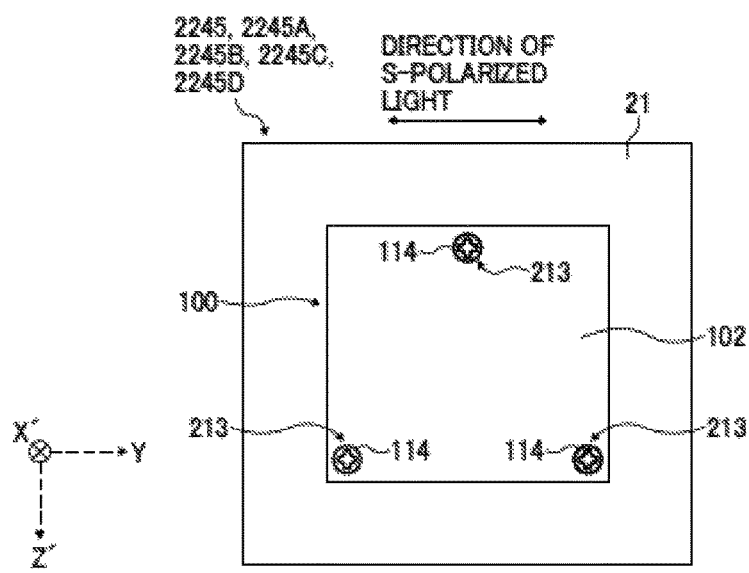
FIG. 20 is a diagram illustrating the fixation structure of an irradiation system in an optical sensor according to a second modification of the present invention.

FIG. 20 is a diagram illustrating the fixation structure of an irradiation system in an optical sensor according to a second modification of the present invention. In the embodiments described above, cases in which the number of the fixed-by-fastening portions 213 between the housing 21 and the circuit board 112 is four are described. However, it is desired that the housing 21 and the circuit board 112 be supported at fewer portions as long as the relative positions of the housing 21 and the circuit board 112 are maintained. This is because compressive stress may be applied to the circuit board 112 and the light source unit 111 depending on the error in the shape of the contacting portions, and a factor in causing an error due to such compressive stress is to be avoided. For example, as illustrated in FIG. 20, it is desired that the planar circuit board 112 be supported at three points, and the number of the fixed-by-fastening portions 213 between the housing 21 and the circuit board 112 may be three.

[Third Modification]

Figure 21:
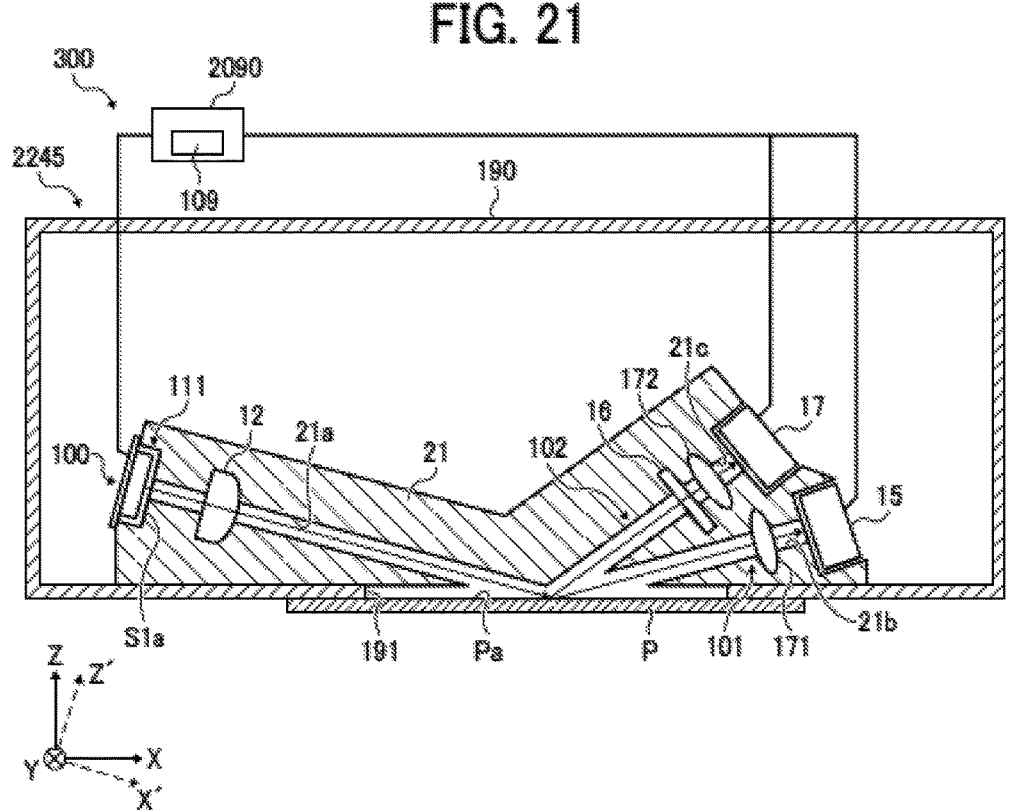
FIG. 21 is a diagram illustrating the configuration of an optical sensor according to a third modification of the present invention.

FIG. 21 is a diagram illustrating the configuration of the optical sensor 2245 according to a third modification of the present invention.

In the embodiments described above, at least one condenser lens that serves as an optical element may be provided before each of the photoreceptors (on the incident side). In particular, FIG. 21 indicates a modification in which condenser lenses 171 and 172 are disposed before (on the incident side of) the photoreceptors 15 and 17 that are elements of the optical sensor 2245 according to the first embodiment.

When such condenser lenses 171 and 172 are disposed before (on the incident side of) the photoreceptors 15 and 17 as described above, the variations in the measurement of the signal levels of the output signals can be reduced. For an optical sensor that discriminates the sheet P based on the reflected light level, the measurement reproducibility is crucial. An optical sensor is installed based on the premise that the surface at which measurement is performed and the surface Pa of the sheet P are on the same plane when measurement is performed. However, the surface Pa of the sheet P may be inclined or floated up from the surface at which measurement is performed due to bending, vibration, or the like, and there are some cases in which the surface Pa of the sheet P and the surface at which measurement is performed are not laid on the same plane. Such a condition leads to changes in the light intensity distribution of the reflected light, and the amount of the received light changes. Accordingly, it is difficult to perform detailed discrimination on a stable basis. In order to avoid such situation, a condenser lens is disposed before each of the photoreceptors. By so doing, the amount of the received light can be stabilized even when the light intensity distribution of the reflected light changes.

As a matter of course, such a configuration in which at least one condenser lens that serves as an optical element is provided before each of the photoreceptors (on the incident side) may be applied to the configuration of the second to fourth embodiments to achieve an effect in a similar manner to the application to the first embodiment.

Alternatively, a photodiode whose light receiving area is sufficiently large may be used as a photoreceptor, or the beam diameter of the irradiation light may be narrowed, in order to deal with the inconvenience caused when the surface Pa of the sheet P and the surface at which measurement is performed are not laid on the same plane.

Moreover, a photodiode where the light receiving area is arrayed may be used as a photoreceptor such that, as a whole, the light receiving area becomes large enough to deal with the amount of shift of the intensity distribution of the reflection light. In this case, even when the intensity distribution of the reflected light shifts, the largest signal among the signals detected by the photodiodes may be used to stabilize the output level of each of the photoreceptors. When a plurality of photodiodes are arrayed, the light receiving area of each one of the photodiodes may be made small so as to reduce the variations in the output caused by the displacement between the incident light and the center of the light receiving area. By so doing, detection that is more accurate is achieved.

The conditions for image formation may be adjusted as follows. Firstly, the relation between the amounts of the specular reflection light of the S-polarized light and P-polarized light and the smoothness, thickness, and basis weight of the sheet P that serves as an object is calculated in advance, and the calculation result is stored in the ROM 2092 of the control circuit 2090 as a database. Secondly, such a database is referred to to determine the smoothness, thickness, and basis weight of the sheet P that serves as an object based on (the signal levels of) the signals output from the optical sensors 2245, 2245A, 2245B, 2245C, and 2245D, and the conditions for image formation are adjusted according to the determined smoothness, thickness, and basis weight of the sheet P.

In the embodiments described above, cases in which there is one sheet feeding tray 2060 is described. However, no limitation in indicated therein, and there may be a plurality of sheet feeding trays 2060. In such cases, it is desired that each of the sheet feeding trays be provided with the optical sensor of the same configuration.

In the embodiments described above, optical sensors are disposed near the sheet feeding tray 2060, and the optical sensors discriminate the brand of the sheet P stored in the sheet feeding tray 2060. However, the positions at which optical sensors are disposed or the timing at which the brand of the sheet P is discriminated are not limited to these embodiments.

For example, the brand of the sheet P may be discriminated while the sheet P is being conveyed. In such cases, the optical sensors 2245, 2245A, 2245B, 2245C, and 2245D are disposed near the sheet conveyance path. For example, the optical sensor 2245 may be disposed in the conveyance path between the sheet feeding roller 2054 and the secondary transfer roller 2042, and the optical sensor 2245 may irradiate the sheet P that is being conveyed towards the secondary transfer unit with light to specify the brand.

Alternatively, the brand of the sheet P may be discriminated before the sheet P is set to the sheet feeding tray 2060. In such cases, the optical sensors are disposed outside the color printer 2000. For example, the optical sensors may be installed on the top surface of the exterior component of the color printer 2000. By way of example, the optical sensor may be designed in a hand-held size like a handy scanner such that an operator can easily handle the optical sensor by hand and the optical sensor becomes detachable from the color printer 2000. In such cases, the operator holds the optical sensor by hand, and manually discriminates the brand of the sheet P using the optical sensor.

In the embodiments described above, it is assumed that an object to be discriminated (estimated, identified) by the optical sensors 2245, 2245A, 2245B, 2245C, and 2245D is the sheet P that is an example of a recording medium. However, no limitation is intended thereby.

In the embodiments described above, the color printer 2000 is used as an example of an image forming apparatus. However, no limitation is intended thereby. For example, a laser printer that forms monochrome images may be used as an image forming apparatus. Moreover, an image forming apparatus other than a printer, for example, a copier, a facsimile, or a multifunction peripheral (MFP) into which these elements are integrated, may be used.

In the embodiments described above, the color printer 2000 that is provided with the four photoconductor drums (2030a, 2030b, 2030c, and 2030d) as image bearers is described. However, no limitation is intended thereby. For example, a color printer for which five photoconductor drums are provided as image bearers may be used as an image forming apparatus.

In the embodiments described above, an image forming apparatus of an intermediate transfer system where a toner image is transferred from the photoconductor drums 2030a, 2030b, 2030c, and 2030d to the sheet P via the transfer belt 2040 is described. However, no limitation is intended thereby. For example, a monochrome or color image forming apparatus in which a toner image is directly transferred from a photoconductor drum to the sheet P may be used.

In the embodiments described above, the optical sensors 2245, 2245A, 2245B, 2245C, and 2245D are applied to an electrophotographic image forming apparatuses where an image is formed on the sheet P using a toner image. However, the optical sensors may be applied to an image forming apparatus in which an image is formed by ejecting ink onto the sheet P.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

What is claimed is:

1. An optical sensor comprising:
    an irradiation system including
        a light source unit having a light source, and
        a circuit board to which the light source unit is attached,
        the irradiation system configured to emit, in a light emitting direction, a linearly polarized light of a first polarization direction onto a surface of an object, in an incident direction inclined with reference to a normal-line direction of the surface of the object;
    a polarizing optical element disposed on an optical path of the light that is emitted from the irradiation system and reflected by diffuse reflection from an incident plane of the object and configured to separate a linearly polarized light component of a second polarization direction from the light emitted from the irradiation system, the second polarization direction being orthogonal to the first polarization direction;
    a first photodetector configured to receive the linearly polarized light component of the second polarization direction separated by the polarizing optical element; and
    a housing supporting the irradiation system, the polarizing optical element, and the first photodetector,
    wherein the circuit board of the irradiation system is fixed in the light emitting direction to a fastening portion of an outside surface of the housing, and
    wherein the light source unit is attached to the circuit board with no direct contact between the light source unit and the housing, and the light source unit protrudes from the circuit board in the light emitting direction of the light source unit via a space.

2. The optical sensor according to claim 1, further comprising a second photodetector disposed on an optical path of light that is emitted from the irradiation system and then is reflected at the object by specular reflection and configured to receive the light reflected by specular reflection.

3. The optical sensor according to claim 2, further comprising at least one third photodetector arranged on an optical path of the light that is reflected by diffuse reflection from the incident plane of the object.

4. The optical sensor according to claim 3, further comprising:
    at least one second optical element disposed on an optical path of the light that is reflected by diffuse reflection from the incident plane of the object and configured to separate the linearly polarized light of the second polarization direction, the second optical element being different than the polarizing optical element; and
    at least one fourth photodetector configured to receive the linearly polarized light separated by the at least one second optical element.

5. The optical sensor according to claim 4, wherein the light source includes a plurality of light-emitting units, the optical sensor further comprising:
    a third optical element disposed immediately after the light-emitting units in an optical path of the light emitted from the irradiation system and configured to separate a portion of the light emitted from the irradiation system, the third optical element being different than the polarizing optical element; and a fifth photodetector configured to receive the portion of the light separated by the third optical element.

6. The optical sensor according to claim 5, further comprising a processor configured to discriminate the object based on a signal output from the first photodetector, a signal output from the second photodetector, a signal output from the third photodetector, a signal output from the fourth photodetector, and a signal output from the fifth photodetector.

7. The optical sensor according to claim 6, wherein the processor controls an amount of light emission of the light-emitting units to a prescribed amount according to a signal output from the fifth photodetector.

8. The optical sensor according to claim 4, further comprising a processor configured to discriminate the object based on a signal output from the first photodetector, a signal output from the second photodetector, a signal output from the third photodetector, and a signal output from the fourth photodetector.

9. The optical sensor according to claim 3, further comprising a processor configured to discriminate the object based on a signal output from the first photodetector, a signal output from the second photodetector, and a signal output from the third photodetector.

10. The optical sensor according to claim 2, further comprising a processor configured to discriminate the object based on a signal output from the first photodetector and a signal output from the second photodetector.

11. A recording medium discrimination device comprising the optical sensor according to claim 10.

12. The optical sensor according to claim 1, wherein the light source includes a plurality of light-emitting units.

13. The optical sensor according to claim 1, wherein the light source unit further includes a package on which the light source is mounted.

14. The optical sensor according to claim 1, wherein the polarizing optical element is disposed on an optical path of the light that is reflected by diffuse reflection in a normal-line direction of the surface of the object.

15. The optical sensor according to claim 1, wherein the housing includes a guide unit configured to restrict movement in a rotation direction of the light source unit around an axis of light emitting direction of the light source unit.

16. A recording medium discrimination device comprising:
an optical sensor including:
an irradiation system including
a light source unit having a light source, and
a circuit board to which the light source unit is attached,
the irradiation system configured to emit, in a light emitting direction, a linearly polarized light of a first polarization direction onto a surface of an object, in an incident direction inclined with reference to a normal-line direction of the surface of the object;
a polarizing optical element disposed on an optical path of the light that is emitted from the irradiation system and reflected by diffuse reflection from an incident plane of the object and configured to separate a linearly polarized light component of a second polarization direction from the light emitted from the irradiation system, the second polarization direction being orthogonal to the first polarization direction;
a first photodetector configured to receive the linearly polarized light component of the second polarization direction separated by the polarizing optical element; and
a housing supporting the irradiation system, the polarizing optical element, and the first photodetector; and
a processor configured to discriminate the object based on a signal output from the optical sensor,
wherein the circuit board of the irradiation system is fixed in the light emitting direction to a fastening portion of an outside surface of the housing, and
wherein the light source unit is attached to the circuit board with no direct contact between the light source unit and the housing, and the light source unit protrudes from the circuit board in the light emitting direction of the light source unit via a space.

17. An image forming apparatus comprising:
an image forming unit configured to form an image on a recording medium; and
a recording medium discrimination device comprising
an optical sensor including
an irradiation system including
a light source unit having a light source, and
a circuit board to which the light source unit is attached,
the irradiation system configured to emit a linearly polarized light of a first polarization direction onto a surface of an object, in an incident direction inclined with reference to a normal-line direction of the surface of the object,
a polarizing optical element disposed on an optical path of the light that is emitted from the irradiation system and reflected by diffuse reflection from an incident plane of the object and configured to separate a linearly polarized light component of a second polarization direction from the light emitted from the irradiation system, the second polarization direction being orthogonal to the first polarization direction,
a first photodetector configured to receive the linearly polarized light component of the second polarization direction separated by the polarizing optical element, and
a housing supporting the irradiation system, the polarizing optical element, and the first photodetector, and
a processor configured to discriminate the object based on a signal output from the optical sensor,
wherein the circuit board of the irradiation system is fixed in the light emitting direction to a fastening portion of an outside surface of the housing, and
wherein the light source unit is attached to the circuit board with no direct contact between the light source unit and the housing, and the light source unit protrudes from the circuit board in the light emitting direction of the light source unit via a space, and
wherein the object is the recording medium.

18. The image forming apparatus according to claim 17, further comprising an adjuster configured to adjust an image-forming condition of the image forming apparatus according to the object discriminated by the recording medium discrimination device.

19. The image forming apparatus according to claim 18, wherein the adjuster discriminates a brand of the recording medium based on a signal level of a signal output from the optical sensor, and adjusts the image-forming condition according to the discriminated brand.

* * * * *